United States Patent
Boyd et al.

(10) Patent No.: US 7,189,242 B2
(45) Date of Patent: Mar. 13, 2007

(54) METHOD AND INSTRUMENTATION FOR VERTEBRAL INTERBODY FUSION

(75) Inventors: Lawrence M. Boyd, Memphis, TN (US); Eddie Ray, III, Cordova, TN (US); Bradley T. Estes, Cordova, TN (US); Mingyan Liu, Bourge la Reine (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 414 days.

(21) Appl. No.: 10/166,306

(22) Filed: Jun. 10, 2002

(65) Prior Publication Data

US 2002/0156481 A1   Oct. 24, 2002

Related U.S. Application Data

(62) Division of application No. 09/287,917, filed on Apr. 7, 1999, now Pat. No. 6,428,541.
(60) Provisional application No. 60/081,206, filed on Apr. 9, 1998.

(51) Int. Cl.
*A61B 17/58* (2006.01)

(52) U.S. Cl. ........................................... 606/90
(58) Field of Classification Search ................ 606/86, 606/96, 105, 61, 90
See application file for complete search history.

(56) References Cited

U.S. PATENT DOCUMENTS

| | | |
|---|---|---|
| 3,620,637 A | 11/1971 | Brown |
| 3,848,601 A | 11/1974 | Ma et al. |

(Continued)

FOREIGN PATENT DOCUMENTS

| | | |
|---|---|---|
| EP | 0260044 | 3/1988 |
| EP | 0646366 | 4/1995 |
| EP | 0739614 | 10/1996 |
| EP | 0796593 | 9/1997 |
| FR | 2739773 | 4/1997 |
| FR | 2767675 | 3/1999 |
| WO | WO 9319678 | 10/1993 |
| WO | WO 9417759 | 8/1994 |
| WO | WO 9612453 | 5/1996 |
| WO | WO 9625103 | 8/1996 |
| WO | WO 9627321 | 9/1996 |
| WO | WO 9627345 | 9/1996 |
| WO | WO 9700149 | 1/1997 |
| WO | WO 9804202 | 2/1998 |

OTHER PUBLICATIONS

"XP–002121982," Section PQ, Week 9524; Derwent Publications Ltd.

(Continued)

*Primary Examiner*—Anhtuan T. Nguyen
(74) *Attorney, Agent, or Firm*—Krieg DeVault LLP

(57) ABSTRACT

A method and instrumentation particularly adapted for disc space preparation from an anterior approach to the spine. In one aspect, an expandable template is provided having guides to guide a cutting device for bilateral formation of openings in the disc space. In another aspect, an improved guide member is provided for guiding a cutting tool. Still further, the invention provides an improved double barrel guide sleeve with a central distraction extension and lateral non-distracting extensions. Optionally, the guide sleeve includes windows and covers to selectively cover the windows. An improved reamer with an internal chamber and optional modular coupling is also provided. A depth stop is provided to selectively engage a tool shaft and a guide sleeve to control tool penetration into the disc space. A method of using the disclosed instruments is also provided.

17 Claims, 23 Drawing Sheets

U.S. PATENT DOCUMENTS

| | | | |
|---|---|---|---|
| 4,341,206 A | | 7/1982 | Perrett et al. |
| 4,566,466 A | * | 1/1986 | Ripple et al. ............... 606/102 |
| 4,834,757 A | * | 5/1989 | Brantigan .................... 623/17 |
| 5,015,247 A | | 5/1991 | Michelson |
| 5,026,373 A | | 6/1991 | Ray |
| 5,055,104 A | | 10/1991 | Ray |
| 5,484,437 A | | 1/1996 | Michelson |
| 5,505,732 A | | 4/1996 | Michelson |
| D374,283 S | * | 10/1996 | Michelson ................. D24/135 |
| D377,093 S | * | 12/1996 | Michelson ................. D24/135 |
| 5,613,489 A | | 3/1997 | Miller et al. |
| 5,632,747 A | | 5/1997 | Scarborough et al. |
| 5,653,762 A | | 8/1997 | Pisharodi |
| 5,669,915 A | | 9/1997 | Caspar et al. |
| 5,700,264 A | | 12/1997 | Zucherman et al. |
| 5,722,977 A | * | 3/1998 | Wilhelmy .................... 606/84 |
| 5,741,253 A | | 4/1998 | Michelson |
| 5,752,969 A | | 5/1998 | Cunci et al. |
| 5,759,185 A | | 6/1998 | Grinberg |
| 5,772,661 A | | 6/1998 | Michelson |
| 5,797,909 A | | 8/1998 | Michelson |
| D401,340 S | | 11/1998 | Waldman et al. |
| D405,176 S | * | 2/1999 | Michelson ................. D24/135 |
| 6,030,390 A | * | 2/2000 | Mehdizadeh ................. 606/84 |
| 6,086,595 A | * | 7/2000 | Yonemura et al. ............ 606/99 |
| 6,159,214 A | * | 12/2000 | Michelson .................. 606/80 |
| 6,228,052 B1 | | 5/2001 | Pohndorf |
| 6,325,827 B1 | * | 12/2001 | Lin ......................... 623/17.16 |
| 2001/0012942 A1 | * | 8/2001 | Estes et al. ................. 606/105 |
| 2004/0068259 A1 | | 4/2004 | Michelson |

OTHER PUBLICATIONS

| | | |
|---|---|---|
| 3,906,996 A | 9/1975 | DePass et al. |
| 4,240,433 A | 12/1980 | Bordow |

"Posterior Lumbar Interbody Fusion with Specialized Instruments," by Gabriel W.C. Ma, MD., F.A.C.S., pp. 57–63.

"The Prefit Dowel Interbertebral Body Fusion as Used in Lumbar Disc Therapy," by B.R. Wiltberger, M.D., pp. 723–727.

"The Dowel Intervertebral–Body Fusion as Used in Lumbar–Disc Surgery," by B.R. Wiltberger, M.D., pp. 284–292.

"Surgical Technique Using Bone Dowel Instrumentation—For Posterior Approach," Sofamor Danek brochure.

"MD–III Threaded Cortical Dowel—Design Rationale and Surgical Technique," University of Florida Tissue Bank brochure.

"Lumbar I/F Cage With VSP Spinal System For PLIF," by John W. Brantigan, M.D.

\* cited by examiner

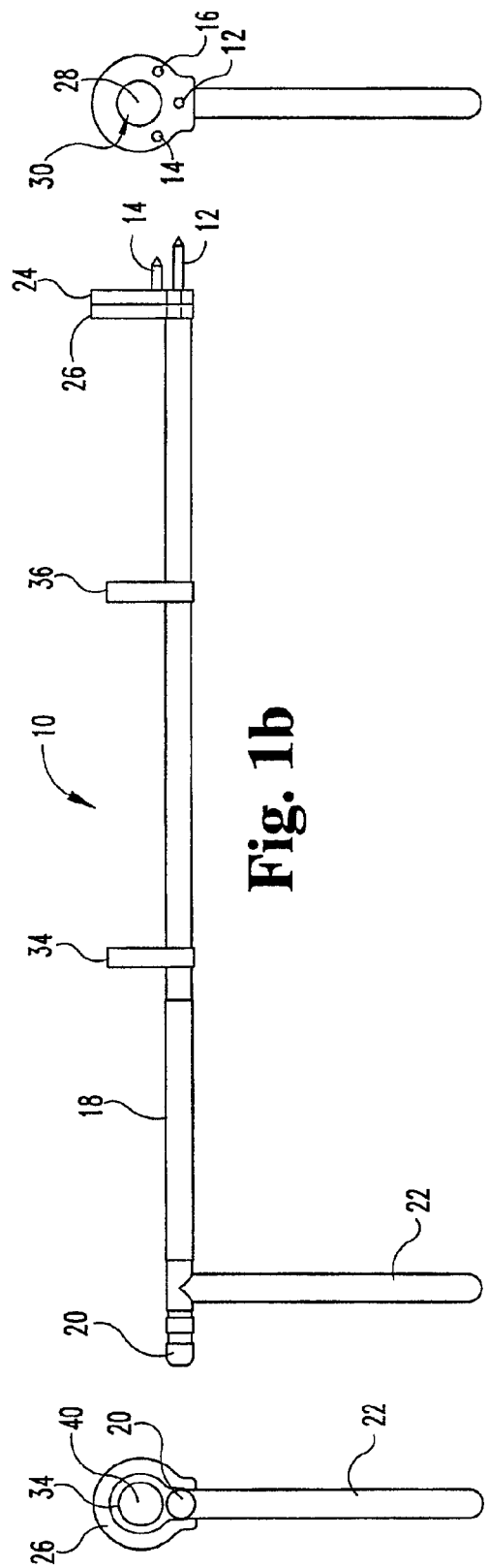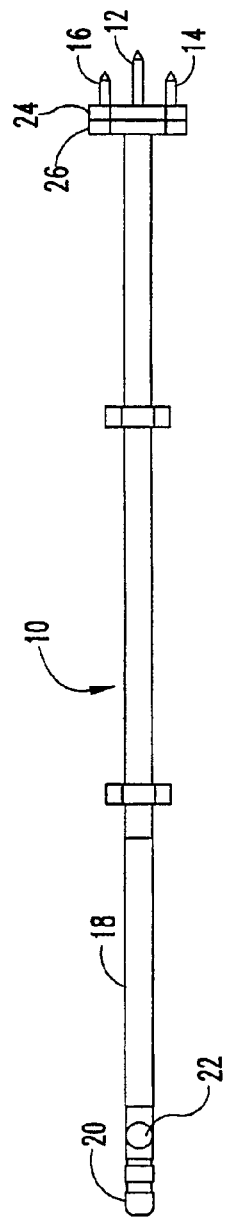

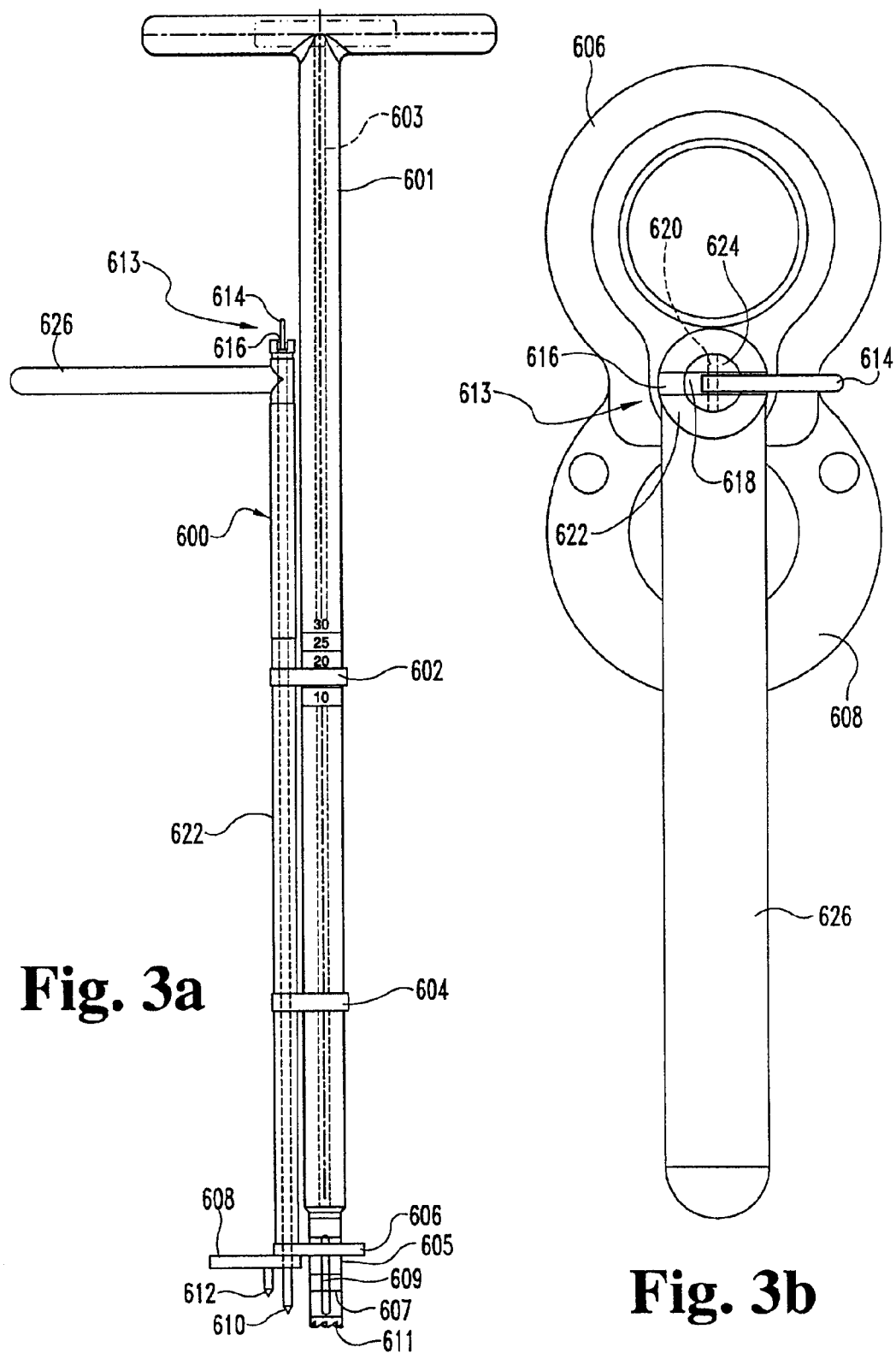

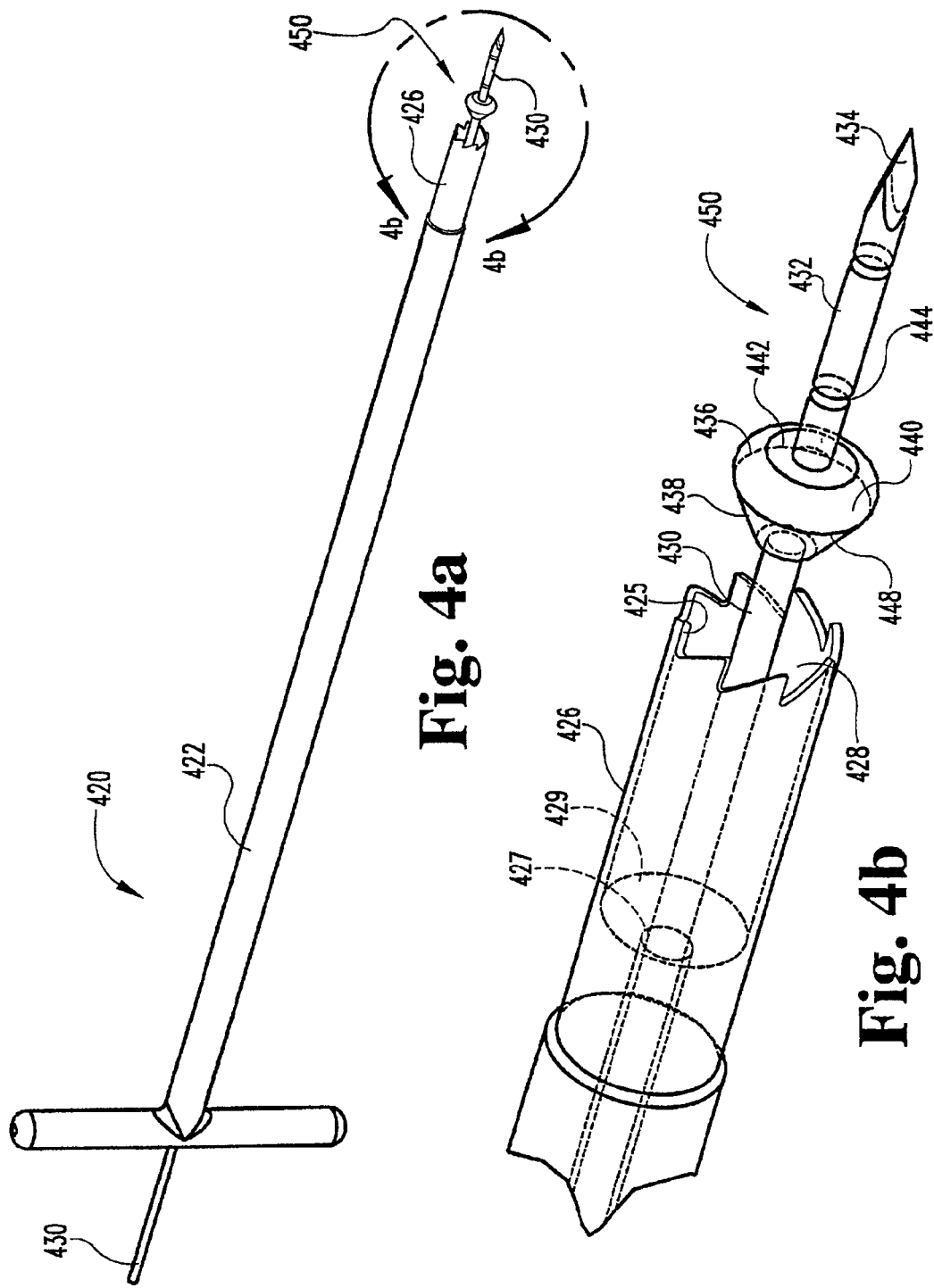

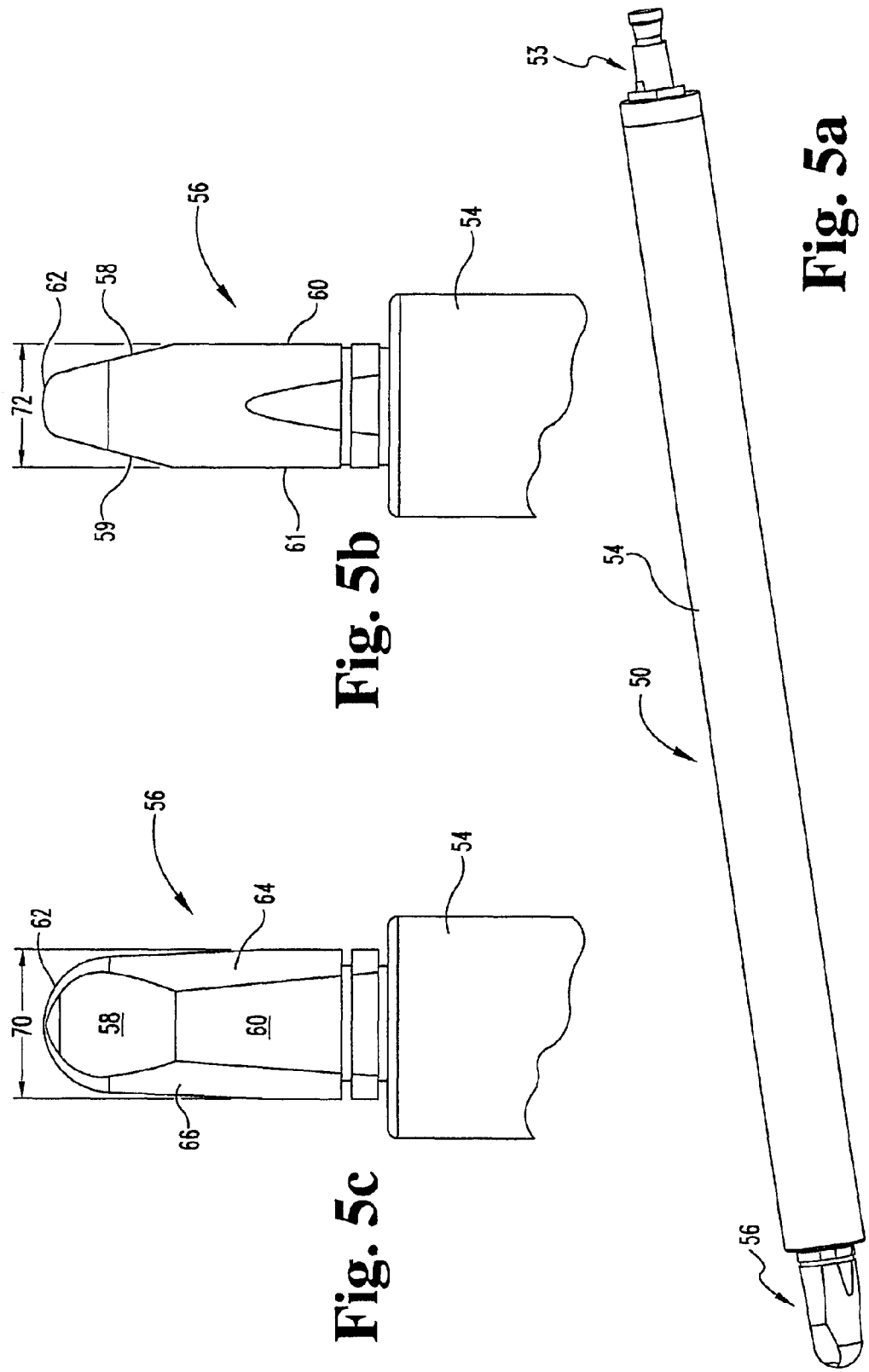

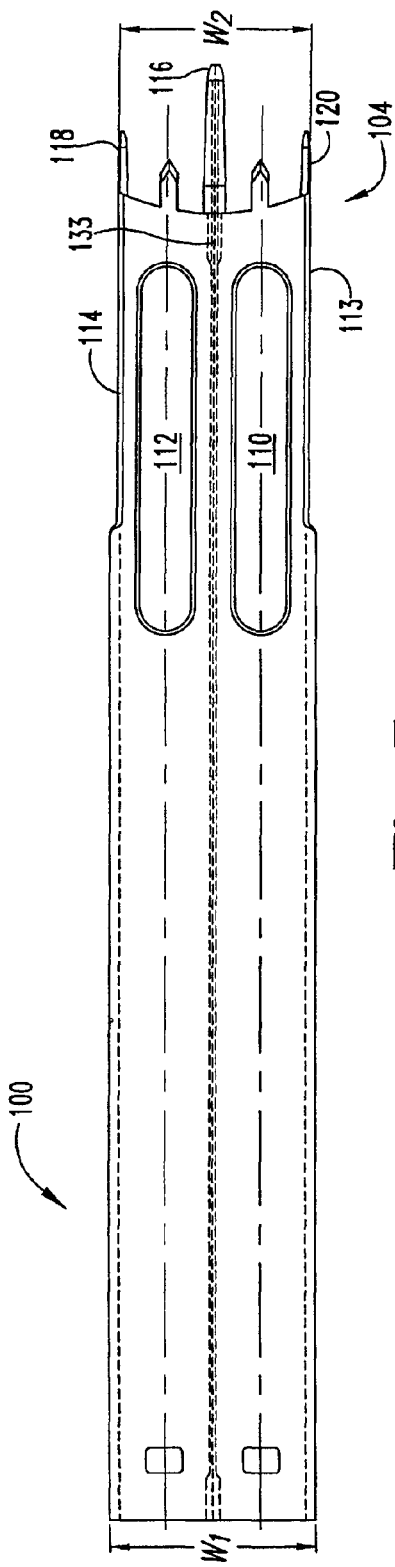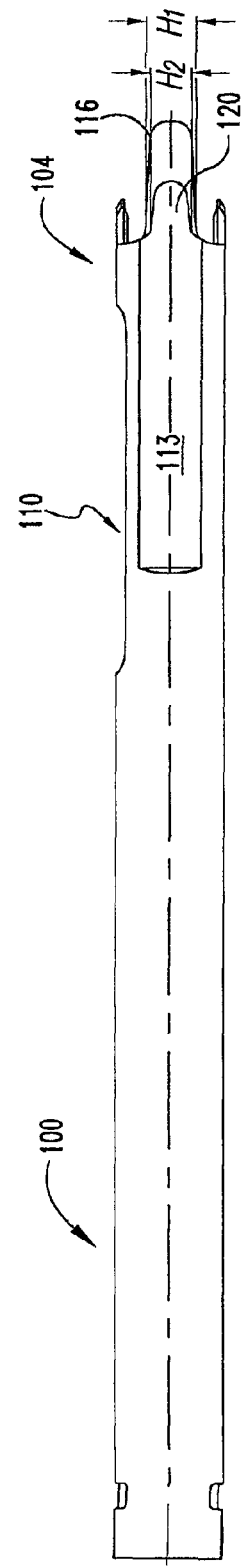
Fig. 7
Fig. 8

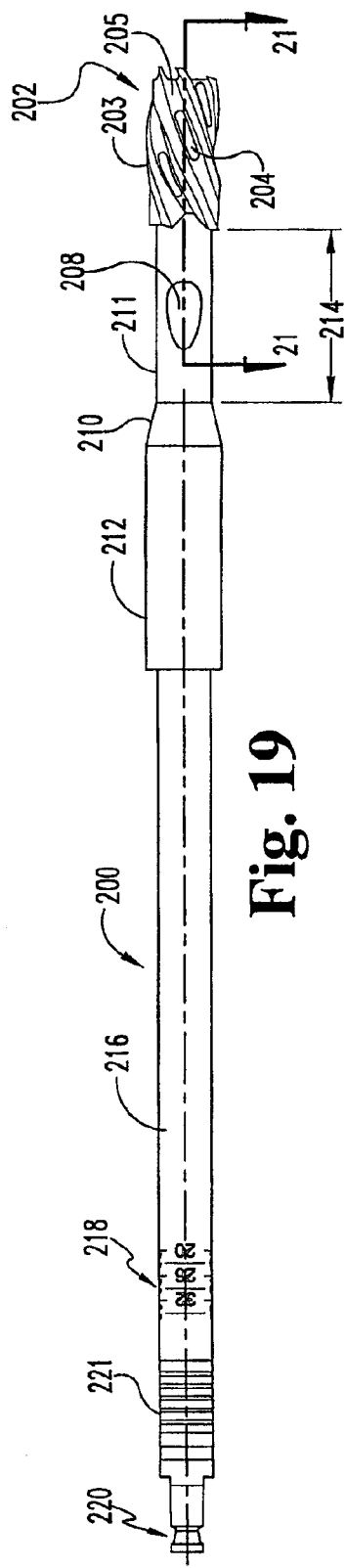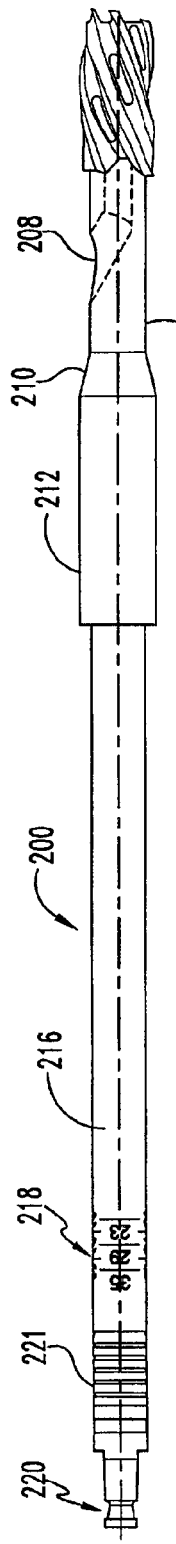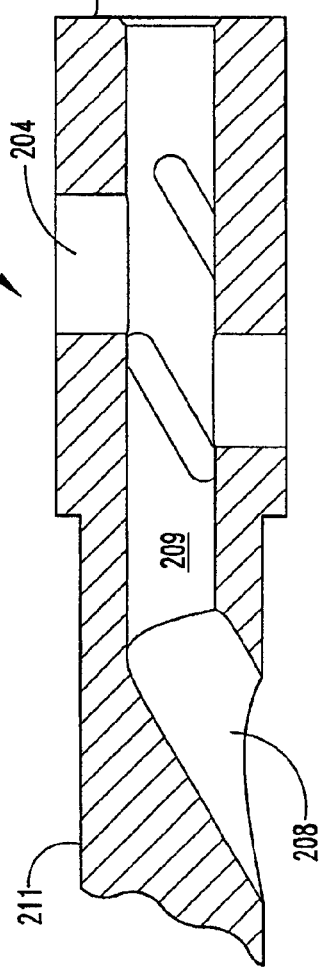

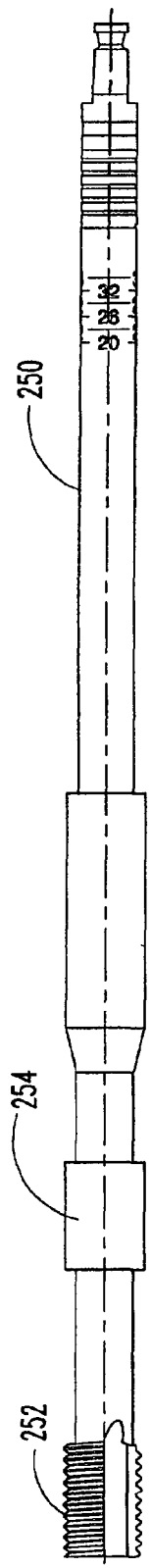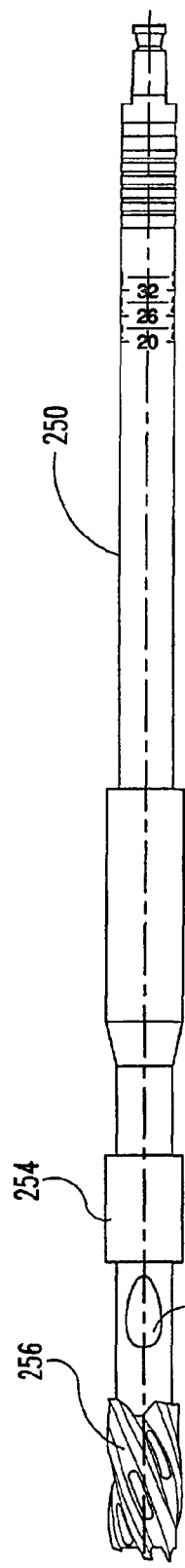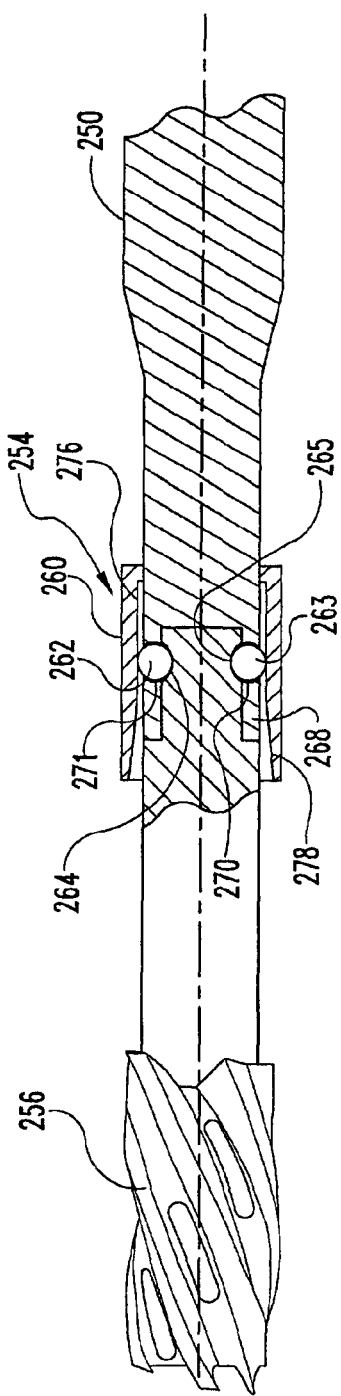
Fig. 25
Fig. 26a
Fig. 26b

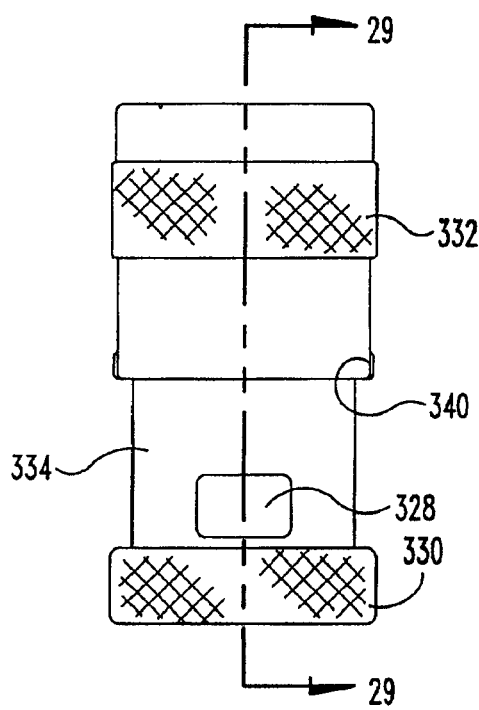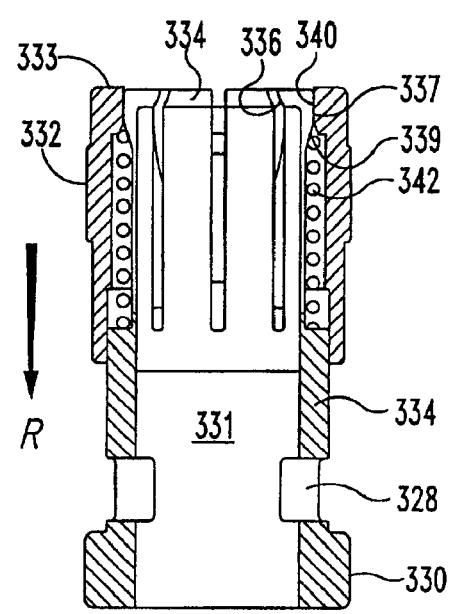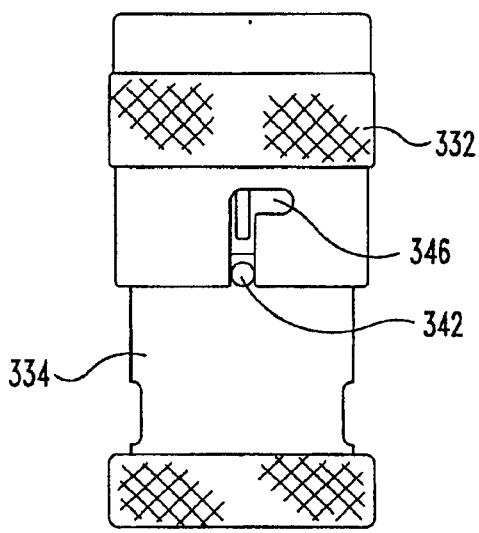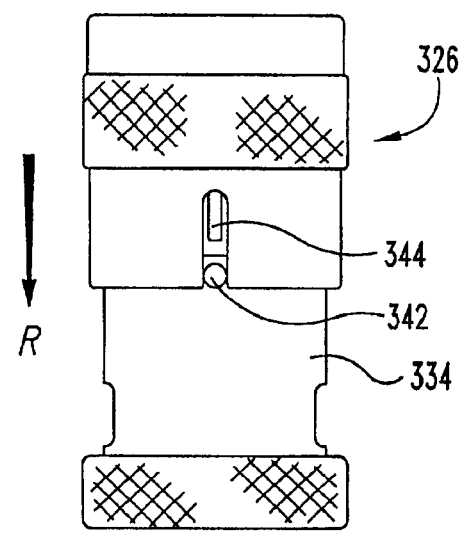
Fig. 28
Fig. 29
Fig. 31
Fig. 30

METHOD AND INSTRUMENTATION FOR VERTEBRAL INTERBODY FUSION

CROSS-REFERENCE TO RELATED APPLICATION

This application is a division of U.S. patent application Ser. No. 09/287,917, filed Apr. 7, 1999, now U.S. Pat. No. 6,428,541 which claims the benefit of U.S. Provisional Application No. 60/081,206, filed Apr. 9, 1998, now abandoned, all of which are incorporated by reference in their entirety.

BACKGROUND OF THE INVENTION

The present invention relates generally to surgical procedures for spinal stabilization and more specifically to instrumentation adapted for inserting a spinal implant within the intervertebral disc space between adjacent vertebra. More particularly, while aspects of the invention may have other applications, the present invention is especially suited for disc space preparation and implant insertion into a disc space from a generally anterior approach to the spine.

Various surgical methods have been devised for the implantation of fusion devices into the disc space. Both anterior and posterior surgical approaches have been used for interbody fusions. In 1956, Ralph Cloward developed a method and instrumentation for anterior spinal interbody fusion of the cervical spine. Cloward surgically removed the disc material and placed a tubular drill guide with a large foot plate and prongs over an alignment rod and then embedded the prongs into adjacent vertebrae. The drill guide served to maintain the alignment of the vertebrae and facilitated the reaming out of bone material adjacent the disc space. The reaming process created a bore to accommodate a bone dowel implant. The drill guide was thereafter removed following the reaming process to allow for the passage of the bone dowel which had an outer diameter significantly larger than the reamed bore and the inner diameter of the drill guide. The removal of the drill guide left the dowel insertion phase completely unprotected.

More recent techniques have advanced this concept and have provided further protection for sensitive tissue during disc space preparation and dowel insertion. Such techniques have been applied to an anterior approach to the lumbar spine. In one approach, a unilateral template has been provided to evaluate the space in the disc space. For bilateral implant placement, the template entire device must be rotated and visually aligned to approximately 180° from the previous position. Thus, there is the chance for operator error in rotating the device to the correct position. Further, there is little guidance to ensure proper alignment of cutting instruments extending through the template.

One approach to provide such alignment is the use of a guide wire extending through a cannulated cutting instrument, such as a trephine. However, for instruments with hollow cutting heads, there is typically no engagement between the inner walls of the hollow cutting head and the guide wire. Thus, the guide wire may bend between the portion extending into the tissue and the guide wire entrance into the cannula of the instrument. As a result, the hollow cutting head may not remain in substantial alignment with the guide wire, resulting in improper opening formation. Therefore, there remains a need for improved guiding mechanisms for cutting instruments.

Once an initial opening or openings have been made in the disc space, the height of the disc space is normally distracted to approximate the normal height. Typically, a first distractor with a height estimated by CT or MRI examination is inserted. If additional distraction is required, the first distractor is removed and a second, larger distractor is inserted. However, since the positioning of the distractors is usually performed without the benefit of protective guide sleeves, the switching of distractors increases the potential for damage to neurovascular structures and may increase the time of the procedure.

For bilateral procedures, a double barrel sleeve may be inserted over a pair of previously placed distractors with a central extension extending into the disc space to maintain distraction. One limitation on guide sleeve placement is the amount of neurovascular retraction that must be achieved to place the guide sleeves against the disc space. For some patients, a double barrel sleeve may not be used because there is insufficient space to accept the sleeve assembly. Further, although the distal end of the sleeve assembly may be configured to engage the vertebral surface, if material has been removed from the disc space, there is the potential that adjacent neurovascular structures may encroach on the working channels in the disc space, resulting in damage to these structures caused by contact with instruments. While visualization windows on the guide sleeve may assist in better visualization of procedure steps and verifying unobstructed working channels prior to tool insertion, the windows themselves may allow tissue to come into contact with instruments in the working channels. Thus, there remains a need for guide sleeves requiring reduced neurovascular retraction for proper placement and providing greater protection to adjacent tissue.

With guide sleeves in place, the disc space and end plates may be prepared for receipt of an implant. Typically, cutting instruments are advanced to remove disc material and bone. Such operations may be time consuming since it is often necessary to adjust depth stop equipment and to remove the instruments to remove cutting debris. Since it is desirable to shorten the time of the operative procedure, there remains a need for improved cutting instruments and depth stop mechanisms.

While the above-described techniques are advances, improvement is still needed in the instruments and methods. The present invention is directed to this need and provides more effective methods and instrumentation for achieving the same.

SUMMARY OF THE INVENTION

The present invention relates to methods and instrumentation for vertebral interbody fusion. In one form, the method contemplates gaining access to at least a portion of the spine, marking the entrance point or points in the disc space, creating an initial opening in the disc space through a template, distracting the disc space and positioning an outer sleeve defining an interior working channel adjacent the disc space. In a preferred embodiment, the template can be inserted in a reduced sized configuration, with a first portion engaging the tissue. The template may then be manipulated to a larger configuration for bilateral insertion procedures by movement of a second portion, without repositioning the first portion. Additionally, a template according to the present invention may include trephine guides that accommodate a variety of different diameter trephine cutting heads. Specifically, trephines according to the present invention may include an upper shaft having a uniform diameter regardless of trephine cutting head diameter. Thus, the upper guides of the template maintain the trephine in axial alignment regardless of whether the lower guide engages the trephine head. In another aspect of the invention, an improved guide member is provided to maintain alignment of cutting instruments.

Once an initial opening or openings have been defined in the disc space, a distractor may be inserted to distract the disc space to the desired height. Various distractors according to the present invention may be used to distract the disc space. One such distractor has a first position that provides a first working distraction height in the disc space and a second position that provides a greater second working distraction height. Should the first working distraction height be insufficient, the distractor according to the present invention may be rotated one quarter turn to create a second greater distraction height in the disc space. Additionally, in a further preferred aspect of the invention, a modular distractor mechanism according to the present invention may be configured to accept many different rotatable distractor tips and may releasable engage the tips such that a distractor tip may be left in the disc space while permitting withdrawal of the distractor tool shaft. With such a configuration, a single distractor tool shaft may be use with various tips, thereby limiting the total number of complete distractor instruments required. Additionally, distractor tips may be made of radiolucent material that will not inhibit x-ray imaging of the disc space. Such distractor tips may include radiographic markers to indicate the ends and/or outer edges of the device and markers to indicate the rotational alignment of the distractors in the disc space.

Once the desired distraction of the disc space has been achieved, the handle of the distractor may be removed and an outer sleeve positioned over the distractor. For a bilateral approach, one or both of the distractors may be left in position and a double barrel sleeve positioned over the distractors and advanced toward the disc space. A further step that may be performed in a preferred embodiment is to select a removable distal tip for the outer sleeve that matches the height of disc space distraction and the diameter of the implant. Thus, an outer sleeve may be used with interchangeable distal tips to accomplish the insertion. Whether single or double, the sleeve is advanced until the leading distractor portion of the outer sleeve is adjacent the disc space. If necessary, a driving cap may be positioned over the proximal end of the outer sleeve. The outer sleeve is then driven into position, preferably with a spike or series of spikes engaging vertebrae adjacent the disc space.

Although various sleeves are known in the art, in a preferred embodiment, outer sleeves according to the present invention have a reduced width portion adjacent the distal end to limit the amount of retraction of the surrounding vascular and neural structures required for the procedure. In a preferred form, a double barrel sleeve assembly includes a central distraction flange having a first height and an opposing pair of lateral extensions having a second height, less than the first height. The lateral extensions provide protection from encroachment of tissue into the working area in the disc space. A further aspect of a preferred embodiment includes the provision of visualization windows along the outer sleeve for visual access to the interior working channel while instruments are in the working channel. Various combinations of windows are disclosed to accomplish the desired visualization. While visualization is desirable, having openings in the outer sleeve may allow surrounding vessels and tissue to migrate into the working channel of the outer sleeve. Tissue and vessels present in the working channel may be damaged by insertion and removal of the tools (often with cutting edges) or during use of those tools. Thus, the present invention contemplates covers over the windows that may be selectively opened for visualization and closed to prevent tissue and vessel infiltration. Additionally, the covers or the outer sleeve may be transparent to allow visualization through the windows without removing the covers or directly through the sleeve. In a similar manner, an image guidance system such as that available under the tradename STEALTH may be used in conjunction with the present system to monitor the advancement and positioning of instruments and implants. Even without the use of an imaging system, the present invention discloses the use of manually adjustable depth stop that may be used to control the steps of trephining, reaming, tapping, and dowel insertion. The term dowel is used in a broad sense throughout the disclosure and is intended to encompass dowels made of bone, metallic cages and other implants used for interbody fusion regardless of shape or material of construction.

One aspect of the present invention comprises an outer sleeve with a visualization window disposed adjacent a distal end and a cover removably covering the window. In one preferred embodiment, the cover includes a flange adjacent the distal end to mobilize vessels and other tissue away from the ends of the outer sleeve. In one form, the cover is slidably disposed on the upper surface of the tube or tubes to cover only the upper windows. In another form, the cover is slidably positioned on the tube to cover the upper and lower windows of the tube.

In yet another aspect, the outer sleeve has a double barrel configuration. The bone engagement end of the outer sleeve includes a first flange having a first height sufficient to maintain distraction. Preferably, the bone engaging end also includes a pair of opposing lateral extensions having a second height less than the first height. The lateral extensions are intended to inhibit lateral encroachment of tissue into the working area in the disc space but are not limited to maintain distraction.

Another aspect of the present invention comprises an adjustable stop mounted on a tool shaft. The stop is selectively engageable with the tool shaft at a plurality of locations along the tool shaft by axial movement of a collar to control the position of the stop engaging portions. With the collar in a first position, the engaging portions are disengaged from the tool space. With the collar in a second position, the engaging portion is urged into engagement with the shaft. The tool shaft is sized to be received within an outer sleeve and the stop is sized to prevent passage within the outer sleeve. Thus, the stop may be selectively coupled to the tool shaft to control the extent of tool shaft that may be received within the outer sleeve. Although not required, in one embodiment the stop includes a viewing window and the tool shaft includes markings, whereby the markings are calibrated to indicate to the user the extent of tool shaft extending beyond a distal end of the outer sleeve.

Still another aspect of the invention comprises a reamer with a reaming head having a plurality of reaming apertures in communication with an internal channel. The internal channel extends within the reaming head and proximally along at least a portion of the reamer shaft. The internal channel includes a proximal segment extending non-parallel to the longitudinal axis of the reamer shaft, whereby reaming debris may be transferred to the exterior of the reaming shaft.

The present invention further contemplates a method for interbody fusion comprising, positioning a template adjacent a fusion site, forming at least one initial opening in the disc space, distracting the disc space, placing a distal portion of an outer sleeve into the disc space, the outer sleeve including at least one visualization window and cover removable disposed over the windows and visualizing the surgical site through the windows. Preferably, the method also includes removing the cover to expose the window prior to visualization. Further, the method may include the step of enlarging the opening with cutting tools and may further include attaching an adjustable depth stop to the tool shaft prior to extension beyond the distal end of the outer sleeve.

Related objects and advantages of the present invention will be apparent from the following brief description of the drawings.

BRIEF DESCRIPTION OF THE DRAWINGS

FIG. 1b is a side elevational view of the template of FIG. 1a.

FIG. 1c is front view of the template of FIG. 1a.

FIG. 1d is a top view of the template of FIG. 1a.

FIG. 1e is a bottom view of the template of FIG. 1a.

FIG. 1f is an enlarged perspective view of the engaging end of the template of FIG. 1a.

FIG. 2b is a top view of the template of FIG. 2a.

FIG. 3a is a side view of another embodiment of an expandable template according to the present invention with a trephine disposed therein.

FIG. 3b is a top view of the expandable template of FIG. 3a showing the locking mechanism.

FIG. 4a is a perspective view of a guide member and trephine according to the present invention.

FIG. 4b is an enlarged perspective view of a portion of FIG. 4a.

FIG. 5a is a perspective view of a distractor according to the present invention.

FIG. 5b is an enlarged front view of the tip of the distractor of FIG. 5a.

FIG. 5c is an enlarged side view of the tip of the distractor of FIG. 5a.

FIG. 7 is a front view of the guide sleeve assembly of FIG. 6.

FIG. 8 is a side view of the guide sleeve assembly of FIG. 6.

FIG. 15b is an end view of the window cover of FIG. 15a.

FIG. 16b is an end view of the window cover of FIG. 16a.

FIG. 19 is a side view of a hollow headed reamer in accordance with another aspect of the present invention.

FIG. 20 is the reamer of FIG. 19 rotated 90 degrees about the shaft longitudinal axis.

FIG. 21 is an enlarged partial cross-sectional view of the head of the reamer of FIG. 19.

FIG. 25 is a side view of a tap having a removable tap head in accordance with another aspect of the present invention.

FIG. 26a is a side view of a reamer having a removable reamer head in accordance with another aspect of the present invention.

FIG. 26b is a partial cross-sectional view of the connection mechanism of FIG. 26a.

FIG. 28 is a side view of the depth stop of FIG. 27.

FIG. 29 is a cross sectional view taken along line 29—29 of FIG. 28.

FIG. 30 is a front view of the depth stop of FIG. 27 with the collar fully extended.

FIG. 31 is a side view of an alternative embodiment of a depth stop in accordance with the present invention.

DESCRIPTION OF THE PREFERRED EMBODIMENTS

Figure 1A:
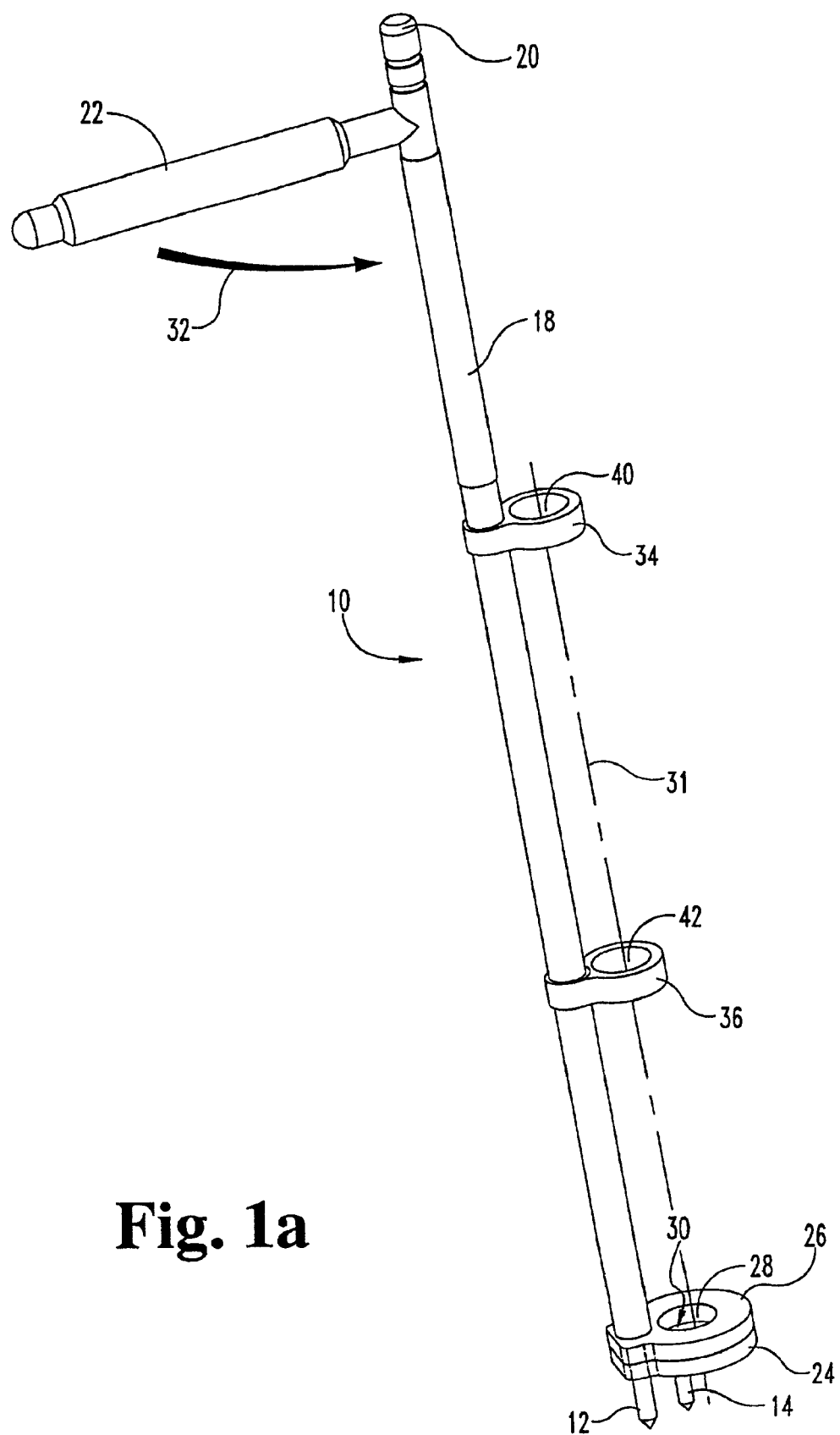
FIG. 1a is a perspective view of an expandable template according to the present invention.
Figure 1F:
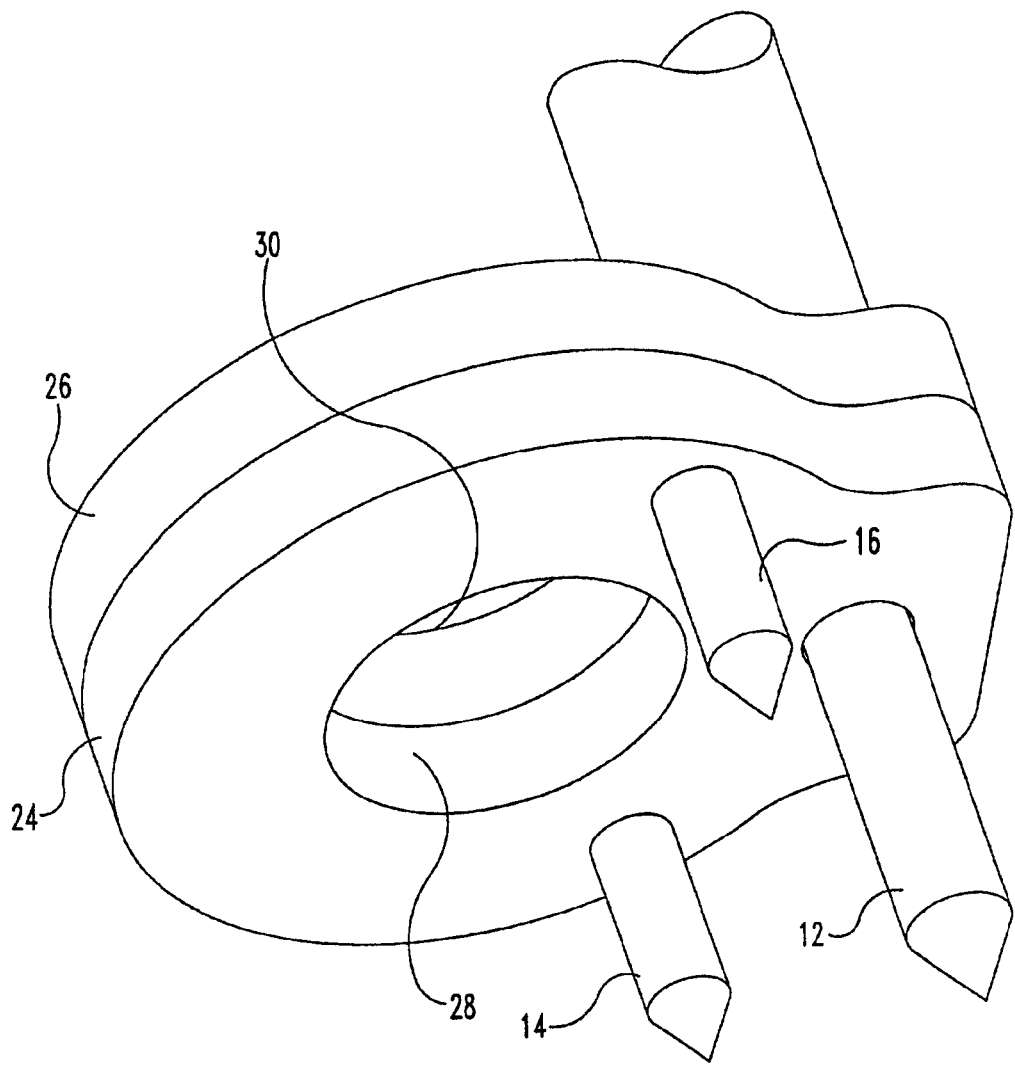

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention relates to methods and instrumentation for performing vertebral interbody fusion. Specifically, although aspects of the present invention may have other uses either alone or in combinations, the instruments and methods disclosed herein are particularly useful for anterior lumbar interbody fusion. Provisional application No. 60/081,206 filed Apr. 9, 1998 is incorporated herein by reference.

Referring now to FIGS. 1(a) through (f), there is shown an intraoperative template 10 for use in interbody fusion. Intraoperative template 10 includes a central anchoring pin 12 and two supplemental anchoring pins 14 and 16. These pins are adapted to be driven into vertebral bodies or other tissue adjacent a disc space to anchor the intraoperative template 10 in the proper location. Template 10 includes an outer shaft 18 interconnected with handle 22 and an inner shaft 20 disposed within outer shaft 18. Inner shaft 20 extends to encompass pin 12. Outer shaft 18 is rotatable with respect to inner shaft 20. Disposed adjacent the distal end of template 10 are guide members 24 and 26 connected to inner shaft 20 and outer shaft 18, respectively. Preferably, guide members 24 and 26 are substantially circular plates having an aperture therein. Guide members 24 and 26 define openings 28 and 30, respectively, adapted to receive a trephine tool therethrough. Trephine guides 34 and 36 are positioned along outer shaft 18 and have openings 40 and 42, respectively, in alignment along axis 31 and are sized to receive a trephine tool shaft. In an alternative embodiment, it is contemplated that inner shaft 20 may be connected to guide member 26 and outer shaft 18 may be connected to guide member 24.

In a first reduced size configuration for unilateral templating and guiding, shown in FIG. 1a, guide members 24 and 26 are axially aligned along axis 31 with openings 28 and 30, respectively, in similar alignment. In this reduced size configuration, the expandable template may be inserted into the body through a relatively small opening and the template may be used for unilateral templating and guiding of a trephine. In this position, a trephine may be guided through guides 34 and 36 and guide members 24 and 26 to engage the tissue below. Moreover, referring to FIG. 3a, a trephine according to the present invention may have a uniform diameter along most of its shaft such that it is a close fit within guides 34 and 36. The close fit in guides 34 and 36 maintains axial alignment, while permitting trephine shaft rotation. Thus, a single template 10 may be used with a variety of sizes of trephine head diameters, provided the shaft has a substantially uniform diameter.

Figure 2A:
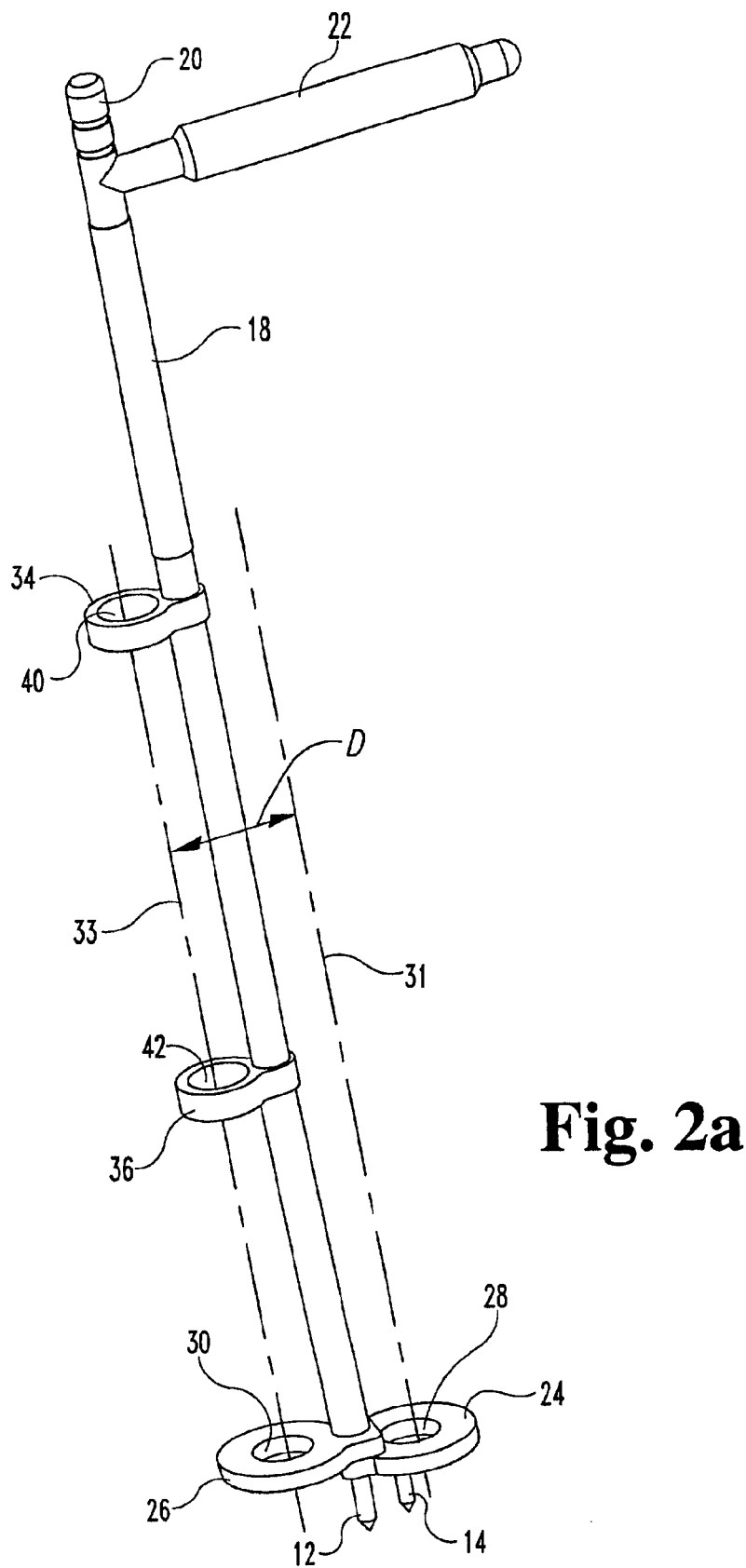
FIG. 2a is a perspective view of the template of FIG. 1a in an expanded condition.
Figure 2B:
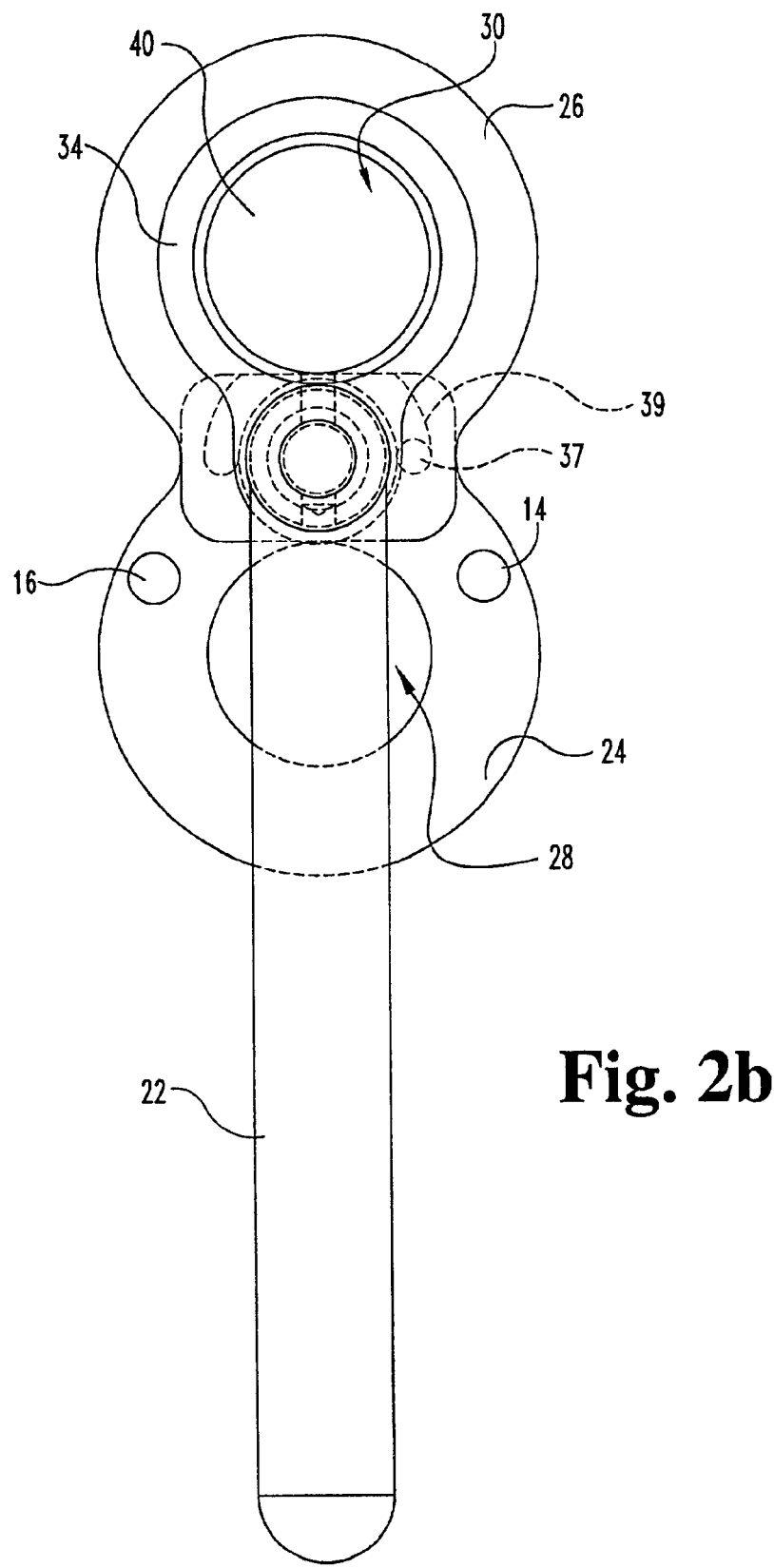

Referring now to FIG. 1a, handle 22 is connected to outer tube 18 and may be rotated in the direction of arrow 32 to a bilateral templating and guiding position. This action rotates outer shaft 18 with respect to inner shaft 20. Guiding member 26, guide 34 and guide 36 are connected to outer shaft 18 and therefore rotate when handle 22 is moved. In contrast, first guide member 24 is interconnected with inner shaft 20 and remains stationary upon rotation of handle 22. As shown in FIG. 2a, handle 22 is rotated approximately 180 degrees to align second template 26 approximately 180 degrees from first template 24 and thereby expand the template to its bilateral trephining position. Thus, a trephine procedure may be conducted along axis 33 through guides 34 and 36 and second member 26 to cut an opening in the disc space. Axis 33 is spaced from axis 31 by a distance "D" representing the distance of spacing of the midpoints between implants to be inserted. FIGS. 2a and 2b show the first and second templates rotated 180 degrees with respect to one another. FIG. 2b shows a top view of a bilateral templating and guiding configuration. In this expanded configuration, the outer edges of guide members 24 and 26 define the total area necessary for placement of implants and instruments having a specific configuration and size. While in a preferred embodiment, cylindrical implants having diameters of 16 mm, 18 mm or 20 mm may be used, it is contemplated that other diameters may be used and other shapes such as, but without limitation, squares and rectangles.

Shown in dashed line in FIG. 2b is a groove 39 formed in guide member 24 and projection 37 defined on guide member 26 and extending into groove 39. It will be understood that the engagement between groove 39 and projection 37 maintains alignment and limits rotation to 180 degrees. Thus, template 10 may be moved between the reduced size configuration and expanded configuration, but the groove and projection engagement limit further movement and will provide a positive indication of 180° rotation, thereby eliminating the requirement for visual alignment with the first position.

Referring now to FIG. 3a, there is illustrated a further embodiment of an expandable template according to the present invention. Template 600 is substantially identical to template 10 previously disclosed above, with the exception that template 600 includes a locking mechanism 613. Expandable template 600 includes a handle 626 connected to outer shaft 622. As in the previous embodiment, template 600 includes a first guide member connected to inner shaft 624 and a second guide member 606 connected to outer shaft 622. First guide member 608 includes spike 612 and inner shaft 624 extends to form central spike 610. Outer shaft includes guides 602 and 604. As shown in FIG. 3a, a trephine 601 may be positioned through guides 602 and 604, and through guide member 606. The cutting head 605 includes cutting teeth 611, a series of index markings 607 and a window 609 to visualize the contents in the hollow interior. Preferably, trephine 601 includes a central cannula 603 extending from the handle to the cutting head.

A locking mechanism 613 is disposed between the inner and outer shafts to prevent rotation. Referring to FIG. 3b, locking arm 614 is pivotally attached to inner shaft 624 by pivot pin 620. The locking arm may be pivoted to extend through slot 616 in the outer shaft and slot 618 in the inner shaft. It will be understood that with locking arm disposed in the slots the inner and outer shaft will be prevented from rotation. In a first locked position, the shafts are aligned as shown in FIG. 1a in the reduced size configuration. In a second locked position, the shafts are aligned as shown in FIG. 3a in the expanded bilateral templating configuration. It will be understood that the expandable, rotatable template of the present invention permits insertion of the device through a smaller opening than would have been permitted with a fixed relation double trephine opening template. Further, the expandable template may be locked in either a unilateral or a bilateral position. Locking engagement in the bilateral position insures accurate bilateral placement with consistency that would not be readily achievable with a unilateral template particularly where the surgeon must reposition the device by visual alignment. Subsequently, the device may be rotated to an expanded configuration suitable for trephine guiding to form bilateral openings without removing the instrument.

In use, access to an anterior portion of the spinal column is achieved by known method. Blood vessels, particularly the aorta, vena cava, and branches thereof are mobilized to provide space for bilateral implant placement. With the template in the reduced size configuration of FIG. 1a, the template is inserted into the body and advanced until the pins are disposed adjacent a disc space. The circumference of the template guide member is selected to the circumference needed for bilateral placement of a pair of implants. More specifically, the area of the guide members of FIG. 2b closely approximate the area needed for placement of the double barrel guide sleeve disclosed herein, see for example FIG. 11. Central pin 12 is disposed centrally between the intended location of the implants. In either the unilateral or expanded bilateral condition, the template may be disposed adjacent the disc space to measure the space available for implant and instrument placement. If the space appears too small, a smaller sized template may be inserted to evaluate the space. In the bilateral condition, the template approximates the area needed for implant and instrument placement. Vessels disposed within the templated area may need to be mobilized outside the area or an alternative implant size or approach may be utilized. Further, osteophytes that appear within the templated area may be removed to prepare for engagement with a guide sleeve. Once the area is cleared, the pins are inserted into the tissue of the disc space and/or adjacent vertebra to anchor the template, thereby maintaining its position during subsequent steps. As shown in FIG. 3a, a trephine is inserted into the guides and through the guiding members. The trephine is cuttingly advanced into the disc tissue to form an opening therein. The trephine may then be at least partially removed from the template to permit movement between the first and second guide members. If a lock mechanism is used, the locking arm must be moved to an unlocked position and the handle rotated to rotate the upper guide member to the expanded bilateral templating position. The trephine is reinserted and advanced through the upper guide member to form a second opening aligned with and offset a distance D from the first opening. Thus, the template permits controlled bilateral opening formation through an expandable and collapsible template. The template may be collapsed into its reduced size form and withdrawn after completion of the trephining operation.

Referring now to FIGS. 4a and 4b, there is shown a further guiding device according to the present invention. Guiding member 450 includes an elongated shaft 430 having a substantially uniform diameter over most of its length. Shaft 430 includes a distal portion adapted for guiding a cutting instrument having a hollow cutting head. The distal portion of shaft 430 includes distal end 432 having a sharpened tip 434 adapted to penetrate tissue, specifically tissue disposed in the disc space. Distal end 432 includes markings 444 which indicate the extent of shaft 430 disposed in the disc space. Although guide member is preferably formed of stainless steel, other bio-compatible materials are contemplated. Specifically, shaft 430 may be formed of a radiolucent material and markings 444 may be radiopaque. Adjacent distal end 432 is enlarged portion 436 having a diameter substantially greater than the shaft diameter. Enlarged portion 436 is adapted to prevent further advancement of guiding member 450 into the tissue and to guide the cutting of the cutting tool. Enlarged portion 436 preferably includes a planar surface 442 substantially perpendicular to the longitudinal axis of shaft 430. A substantially spherical surface 440 is disposed adjacent planar surface 442. This is followed by a tapering conical surface 438 that is adapted to align the cutting head over enlarged end 436. It will be understood that the internal surface of cutting head 426 defining opening 428 engages the transition line 448 between spherical surface 440 and taper surface 438. The diameter of transition line 448 substantially matches the internal diameter of cutting head 426 to provide a close fit for maintaining alignment.

In use, guide member 450 is inserted into the body with distal end 432 fully inserted into the tissue of interest, preferably disc tissue although other uses are contemplated. Cutting tool 420 is advanced over guide member 450 with shaft 422 in substantial alignment with shaft 430 extending through channel 427. While a trephine is illustrated, other cutting tools such as, but without limitation, reamers and non-rotary cutting tools may be used with guide members according to the present invention. Cutting teeth 425 are positioned adjacent enlarged portion 436 and are advanced until the cutting teeth surround the enlarged portion. It will be understood that if cutting teeth are offset with respect to enlarged portion 436, the teeth will engage a portion of conical surface 438 and thereby be urged into alignment. Enlarged portion 436 is received within chamber 428 and cutting teeth 425 are advanced along distal portion 432 until conical surface 428 abuts internal conical surface 429 to prevent further advancement. The assembly may be withdrawn with the cut tissue impaled by distal portion 432. The tissue may be removed from chamber 428 by advancing the guide member with respect to the cutting head such that the enlarged portion urges the tissue out of the hollow interior. This may be particularly helpful where the cutting tool is used to extract a bone graft. The depth of cutting teeth penetration may be adjusted by placement of the enlarged portion. Additionally, while only a single enlarged portion is shown, more than one may be positioned on the shaft to further adjust the guide member depth and cutting depth of the tool.

Referring now to FIGS. 5a–c, there is shown a disc space distracter 50 according to one aspect of the present invention. Distractor 50 includes a proximal end 53 configured as an enlarged end for engagement with a conventional Hudson connection on a T-handle (not shown). Shaft 54 is joined with a distracter tip 56. While an integral shaft and head are shown, head 56 may be removably attached to shaft 54. One such removable attachment is more fully disclosed in provisional application No. 60/081,206 incorporated herein by reference. Distracter tip 56 is designed such that it can be inserted in a disc space to establish a first working distraction height 72 (see FIG. 5b), which is less than a second working distraction height 70 (see FIG. 5c). More specifically, distracter tip 56 has a rounded leading edge 62 that extends to opposing inclined surfaces 58 and 59 which extending more proximally blend into substantially planar opposing surfaces 60 and 61, respectively. Planar surfaces 60 and 61 extend in parallel alignment along the longitudinal axis of the distracter to establish height 72. It will be understood that the inclined surfaces 58 and 59 cooperate to ease insertion into the disc space and to initially distract the disc space to at least a height 72. If first height 72 is sufficient, further procedures as known in the art may then be carried out to accomplish implant insertion. Alternatively, rounded leading edge 62 permits the distractor to be inserted to directly achieve second distraction height 70.

In an alternative aspect, should first height 72 be insufficient, head 56 may be rotated a quarter turn, or 90 degrees, to the position shown in FIG. 5c. Rounded surfaces 64 and 66 engage the bone to urge it apart and into a second larger distracted height 70. It will be understood that utilization of a distracter tip as disclosed in the present invention, permits a two-height distraction of the disc space that may be carried out with a single instrument and without removing the instrument from the disc space. This offers an advantage to the surgeon of a single instrument offering multiple useful distraction heights. Thus, a surgeon may initially believe a disc space will need a first amount of distraction. After insertion of the distractor, the surgeon may discover that further distraction is required. In this situation, a distractor according to the present invention allows further disctraction without instrument withdrawal. Moreover, distractor head 56 limits the number of instruments that must be made available to surgeon to accomplish a surgical procedure by providing two working distraction heights on a single tool. Specifically, but without limitation, the distraction heads may be formed with first heights 72 ranging from 6 mm to 12 mm and second heights ranging from 7 mm to 13 mm. Preferably, heights 70 and 72 vary by 2 mm increments. More preferably, height 72 is 8 mm and height 70 is 10 mm. In another form, height 72 is 10 mm and height 70 is 12 mm. Other variations may be utilized that provide multiple working distraction heights that approximate the disc height in a normal spine.

Figure 6:
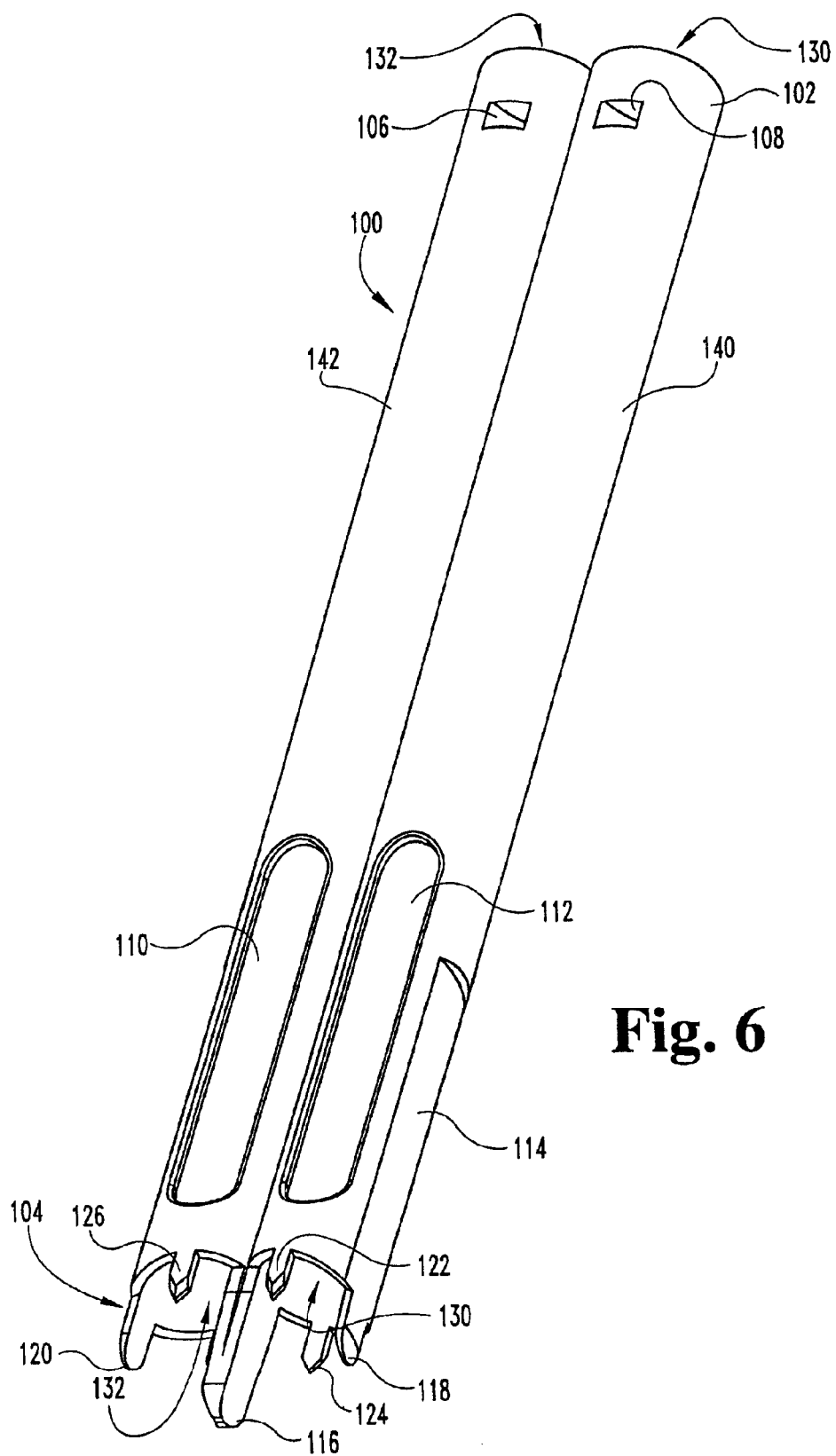
FIG. 6 is a perspective view of a guide sleeve assembly according to another aspect of the present invention.

Referring now to FIG. 6, there is shown a double-barrel guide sleeve assembly 100 having a first sleeve 140 connected to a second sleeve 142. Sleeves 140 and 142 each define working channels 130 and 132 extending in a substantially unobstructed manner from the proximal end 102 to distal end 104. Assembly 100 includes upper windows 106 and 108 formed in sleeves 142 and 140, respectively, that are adapted for engagement by a removal tool. The sleeves also include lower elongated visualization windows 110 and 112.

Adjacent distal end 104, the material thickness along the outer edge of each tube 140 and 142 is reduced in order to provide a smaller cross-sectional area for the sleeve assembly as well as a reduced width extending transverse to the longitudinal axis of assembly. The reduced cross-sectional area and smaller width reduces the amount of retraction of vessels adjacent the disc space that would be required without the reduction. Side wall 114 is shown as an indication of the reduced thickness of the device in the distal area 104.

Distal end 104 includes a central distracting flange 116 which may be inserted into the disc space to achieve or maintain a height H1 of distraction between two vertebral bodies. Lateral flanges 118 and 120 also extend partially into or adjacent to the disc space. However, in a preferred embodiment, lateral flanges 118 and 120 have a height H2 that is less than height H1. Thus, they do not provide distraction of the disc space but are provided primarily to protect surrounding vessels and neurological structures from damage during the procedures. Although that is the function of the lateral flanges in the preferred embodiment, it is contemplated that they could be sized to provide distraction within the disc space in conjunction with central flange 116. Additionally, distal end 104 includes spikes 122, 124, 126, and a fourth spike which is not seen in the view of FIG. 10. These spikes may be urged into the bone of the adjacent vertebral bodies to hold the double-barrel guide sleeve 100 in a fixed position relative to the vertebral bodies. It will be understood that windows 110 and 112 provide the medical staff with the opportunity to visualize the instruments as well as the openings in the disc space and vertebral bodies, without entirely removing instrumentation from guide sleeve 100.

Referring more specifically to FIG. 7, double-barrel guide sleeve 100 is shown in a front view to further illustrate an additional aspect of the invention. Opposite vertebrae engaging end 104, the guide sleeve has a width W1 approximately twice the diameter of one of the sleeves. Adjacent vertebrae engaging end 104 of the sleeve, each of the outer portions of the sleeves has a reduced wall thickness at side walls 114 and 113. The walls are not entirely flat but have a substantially greater radius of curvature (see FIG. 11) giving the appearance of substantially flat walls but providing a reduction in wall thickness over a greater area and tapering to the full wall thickness at the termination of side walls 113 and 114. The reduced wall thickness on the lateral portion of each tube reduces the overall width of the device to a width W2. The reduction in width decreases the amount of retraction that vessels in the area must be moved. The desirable reduction in width is accomplished with little reduction in the strength of the device since much of the structural integrity, particularly resistance to axial compression during insertion of the sleeves, is carried by the much thicker central portion where the two sleeves are joined to each other. Preferably, the central portion may have a thickness equal to two tube wall thickness.

Figure 9:
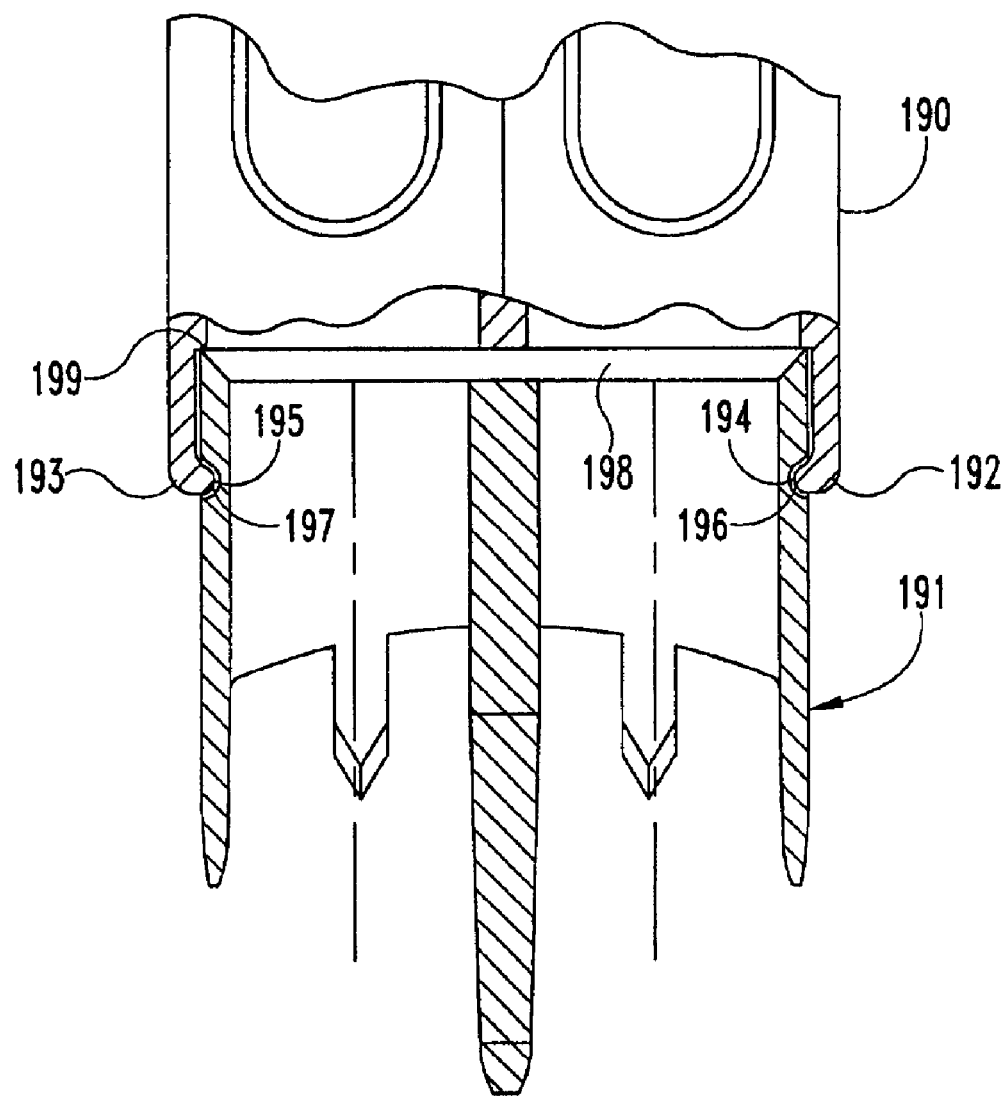
FIG. 9 is a partial cross-sectional side view of a guide sleeve assembly with a removable tip.

As a further alternative, FIG. 9 shows that guide sleeve assembly 190 may be provided with removable barrel tips 191 having different distraction heights, lateral extensions, or spike patterns. Barrel tips may also have different diameters corresponding to the placement of implants with different diameters. Removable tips 191 may be held in place by any of a variety of known connection mechanisms. However, in a preferred embodiment, guide sleeve assembly 190 includes a pair of opposing flexible fingers 192 and 193 having projections 194 and 195, respectively. Projections 192 and 193 on the flexible fingers extend into grooves 196 and 197, respectively, defined in the removable tip. To limit proximal movement of tip 191 during insertion, tapered surface 198 abuttingly engages shoulder 199 and the central portion between the upper guide tubes. Use of a removable tip according to the present invention not only allows use of interchangeable tips to suit a specific application, it also permits removal of the outer sleeve after placement in the body. With only tip 101 in place, the posterior aspect of the disc space or spinal canal may be more easily visualized and accessed.

Figure 10:
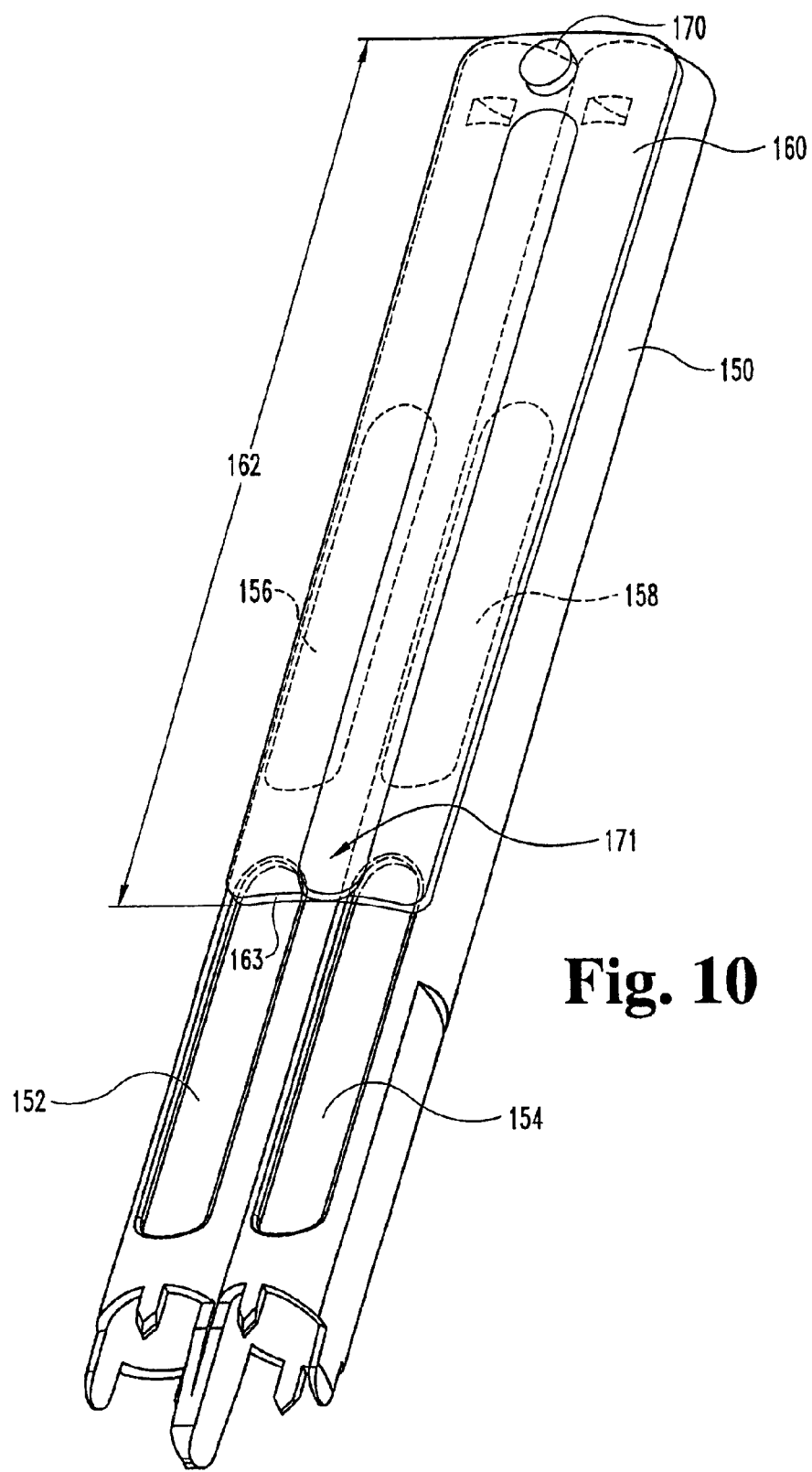
FIG. 10 is a perspective view of a guide sleeve assembly with a cover according to the present invention.
Figure 11:
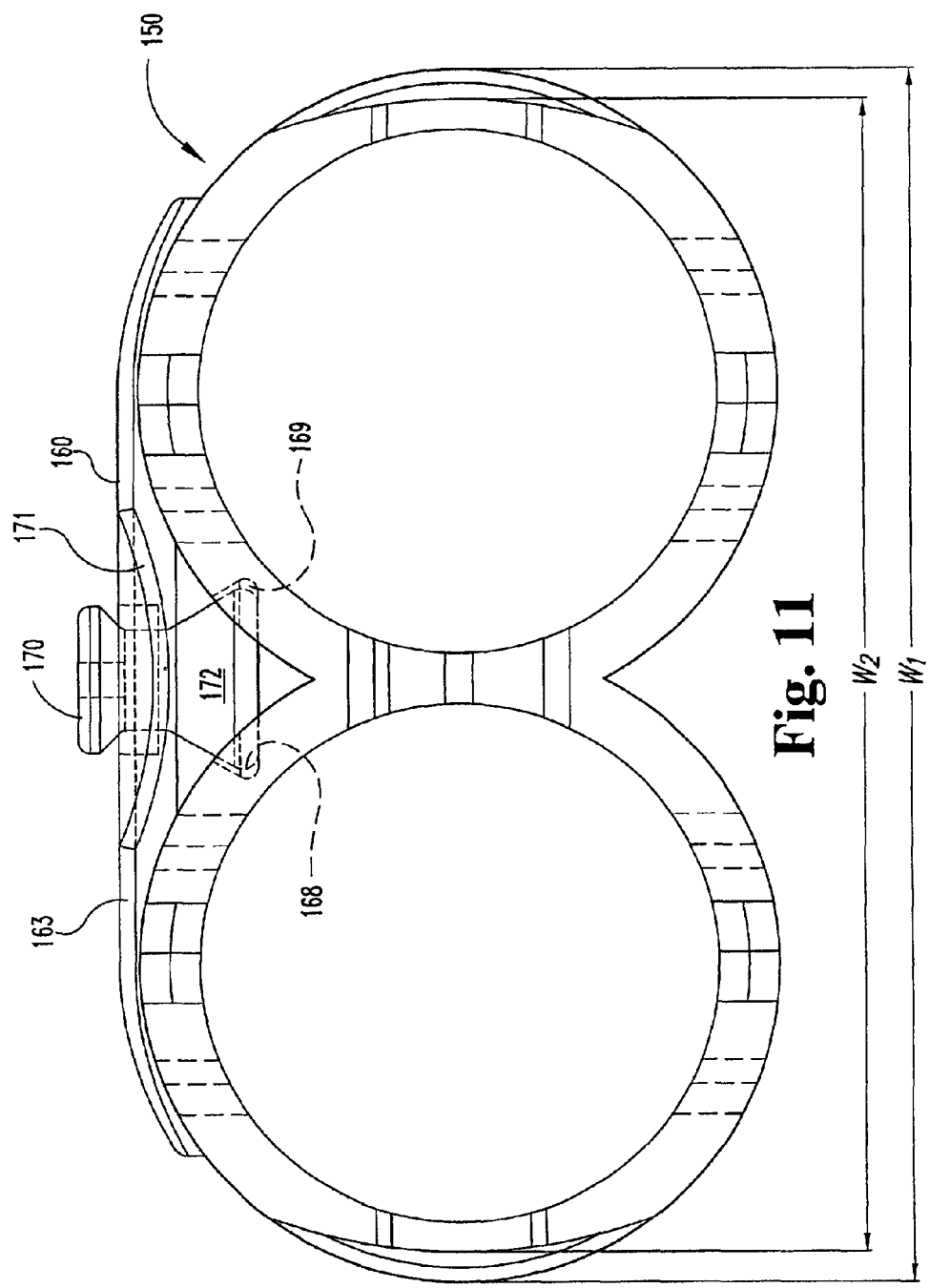
FIG. 11 is an end view of the guide sleeve assembly of FIG. 10.

Referring now to FIGS. 10 and 11, there is shown a further embodiment of a double-barrel guide sleeve similar in most respects to outer sleeve 100 of FIG. 6. The further embodiment of FIG. 12 differs from that of FIG. 6 in that guide sleeve 100 included only a single elongated visualization window for each sleeve. In double-barrel guide sleeve 150, each sleeve has a total of four windows, two on an upper surface and two on a lower surface. Thus, as shown in FIG. 10, windows 152, 154, 156, 158 provide the surgeon with the opportunity for visualization along the majority of each working channel. The back side of guide sleeve 150 has a similar configuration.

Guide sleeve 150 is used in a similar fashion to the outer sleeve 100. In a preferred embodiment, outer sleeve 100 is provided with a cover 160 having a length 162 sufficient to cover all four windows disposed on at least one side of the device. Cover 160 is provided to prevent possible damage to tissues which may invade the working channel through the windows and be damaged by the operation, insertion or removal of tools in the working channels. It is contemplated that cover 160 may be transparent to allow visualization directly through the cover or that it could be opaque, requiring that the cover be repositioned prior to visualization. It is further contemplated that the cover may have a length 162 sufficient to extend over all the windows on one side and it may be able to selectively cover either proximal windows 156 and 158 or all of the windows. Leading edge 163 is tapered to prevent damage to tissue, particularly when moving forward to cover the windows. The taper should urge the tissue out and away from the guide sleeve. Further, cover 160 includes a dip 171 substantially following the contour between the pair of guide sleeves.

Although other attachment mechanisms are contemplated, as shown in FIG. 11, cover 160 is held in place by retaining pin 170 connected through cover 160 to a lower dovetail portion 172. Dovetail portion 172 is slidable along a dovetail groove defined by grooves 168 and 169 defined within the outer body of guide sleeve 150.

FIGS. 10 and 11 show one embodiment of a cover for slidably and selectively covering a plurality of windows in outer sleeve 150. FIGS. 12 through 16b illustrate yet further embodiments of a cover which may be displaced to expose underlying windows in one of the double-barrel tubes. Further, although the covers are disclosed for use with double barrel assemblies, it is contemplated that they may be used with single tube guide sleeves without undue modification. In the further embodiments, the working channel and visualization windows of one barrel may be exposed while a cover remains in place on the alternate barrel.

Figure 12:
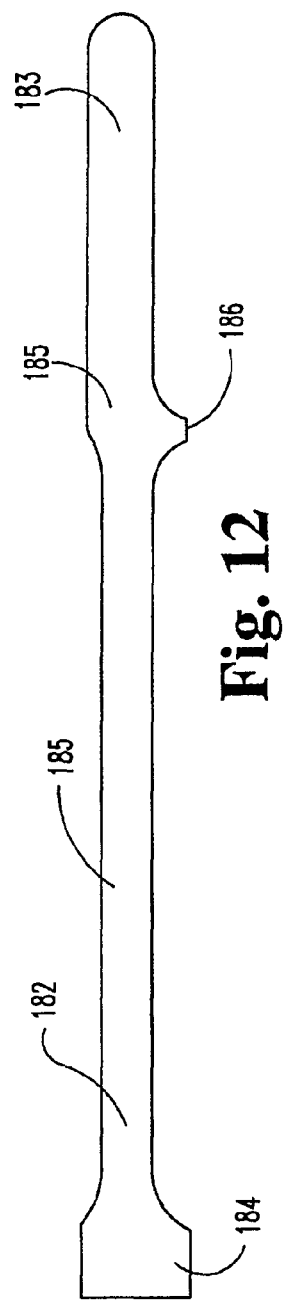
FIG. 12 is a front view of one embodiment of a guide sleeve window cover according to the present invention.
Figure 13:
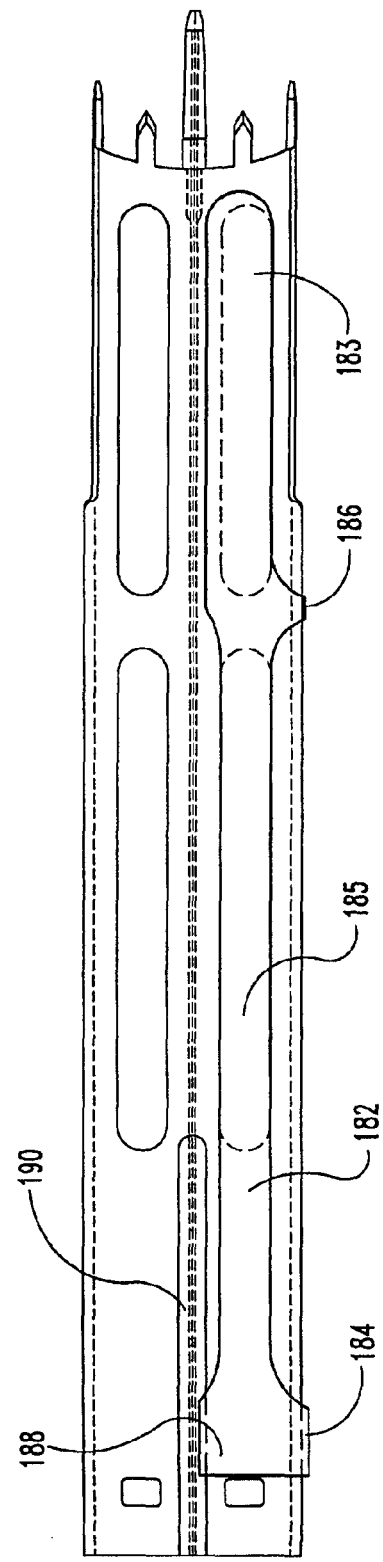
FIG. 13 is a front view of a guide sleeve assembly with the cover of FIG. 12 mounted thereon.

Referring to FIG. 12, partially cylindrical cover 182 consists of elongated portions 183 and 185 which are sized to cover underlying visualization windows. The elongated portions are retained on the guide sleeve by connectors 184 and 186 that are sized to extend around the exterior of the outer tube and guiding portion 188. It is contemplated that connectors 184 and 186 may engage a cover portion on the oppostie side of the guide sleeve identical to that shown in FIG. 12. While cover 182 is disclosed as having elongated members 183 and 185 interconnected, it is contemplated that each of the covers 183 and 185 could be separate to allow visualization of the windows only on an upper or lower surface of the working tube without opening the opposing window.

Figure 14:
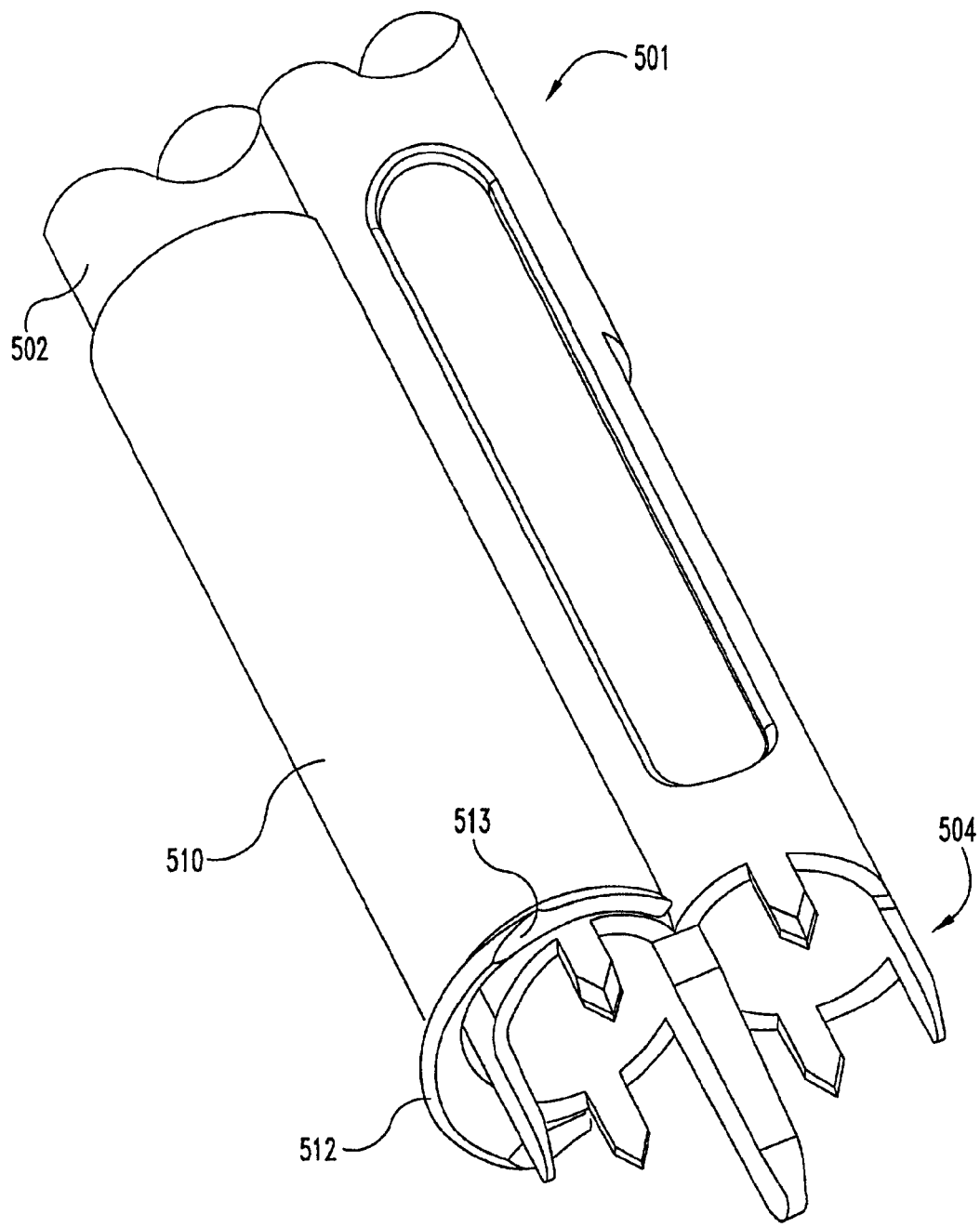
FIG. 14 is a perspective view of an engaging end of a guide sleeve assembly with another embodiment of a window cover according to the present invention.
Figure 15B:
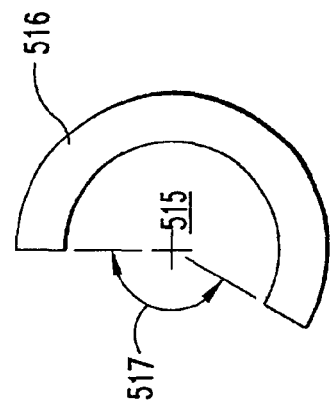

Referring to FIGS. 14 through 16b, there are shown still further embodiments of window covers according to the present invention. FIG. 14 shows a cover 510 that covers approximately 200° of a single sleeve 502 of a guide sleeve assembly 501 similar to that of FIG. 6. The cover includes an internal passage 515 and is slidable along sleeve 502. In a further aspect, cover 510 includes an enlarged flange 512 adjacent bone engaging end 504. Tapered surface 513 extends between flange 512 and the outer diameter of cover 510. Referring to FIGS. 15a and 15b, cover 514 includes a flange 516 that extends along the entire leading edge of the cover. The cover extends in a partial cylinder lacking material over angle 517.

Angle 517 is approximately 160°, thus material extends around approximately 200° of the cylindrical shape. It will be understood that covers 510, 514, and 520 may be configured to have material extending less than 200° around the cylinder to allow rotation of the cover in relation to a guide sleeve such that the cover may be rotated to uncover a window. Thus, for covers 510 and 514, the flanges may continue to hold the vessels away from the guide sleeve even when moved to allow access through one of the windows.

Figure 16B:
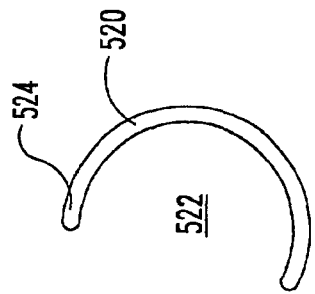
Figure 15A:
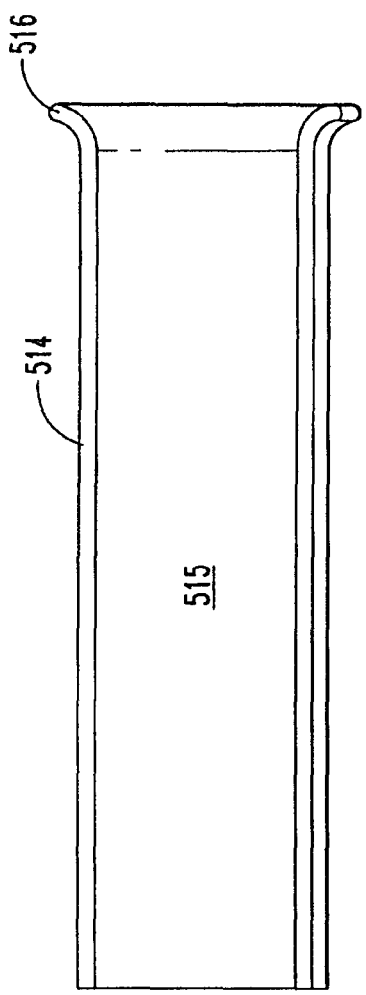
FIG. 15a is a side view of a window cover.
Figure 16A:
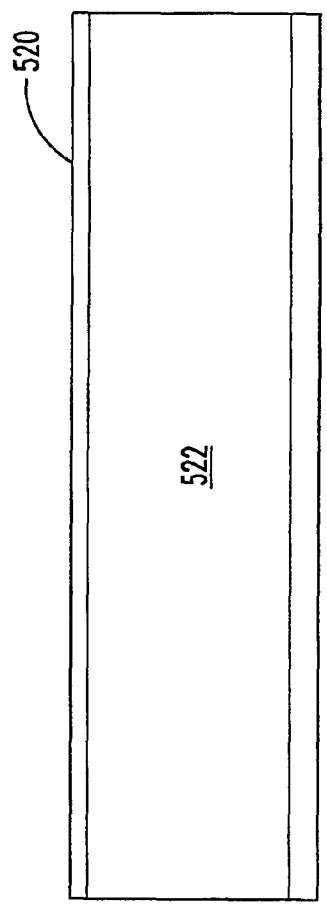
FIG. 16a is still a further embodiment of a window cover in accordance with the present invention.

An alternative embodiment shown in FIGS. 16a and 16b does not include the enlarged flange 512. Cover 520 has a uniform end 524 and defines an internal channel 522 adapted to receive a guide sleeve. However, in certain surgical procedures it is desirable to use the embodiment having the flange to protect closely adjacent vessels and to urge them away from the distal end of the guide sleeve where it might be possible to contact instruments disposed therein. Without the use of a cover, the outer sleeves may not match the shape of the surface of the vertebral body thereby allowing the potential for contact between instruments in the outer sleeves and closely adjacent vessels. This is particularly dangerous when operating close to the vena cava and aorta. However, as shown in FIGS. 17 and 18, the flanges on the covers act as a retractor to urge the vessels away from the outer sleeves.

Figure 17:
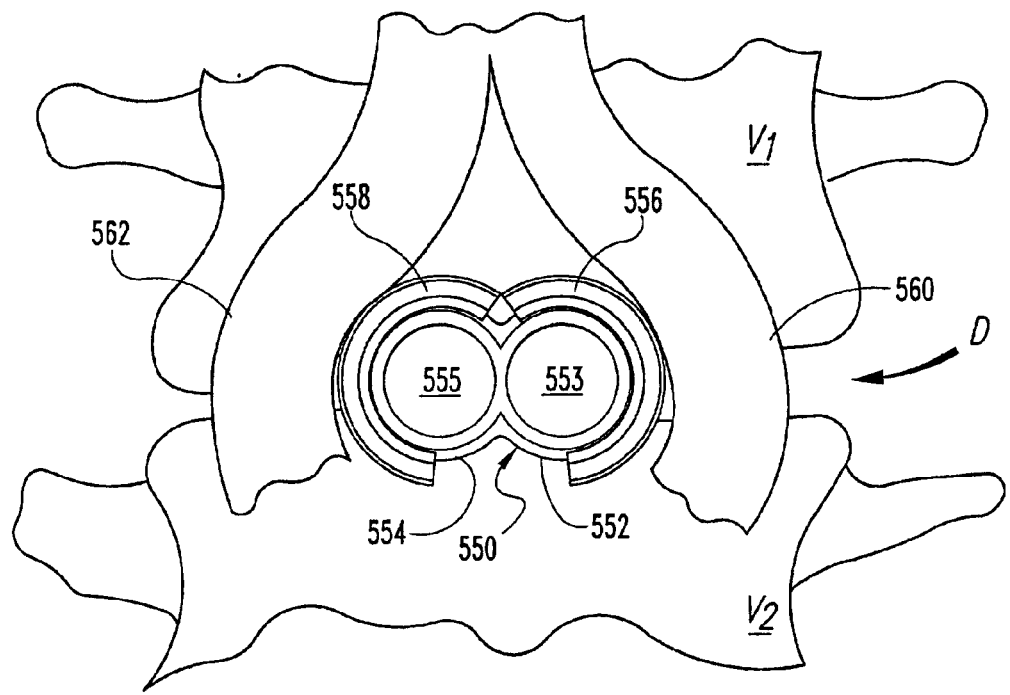
FIG. 17 is an anterior to posterior view of a guide sleeve assembly with window covers according to FIG. 15 disposed thereon, the guide sleeve assembly is positioned in relation to a pair of adjacent vertebral bodies and blood vessels.

Referring more specifically to FIG. 17, guide assembly 550 is illustrated as being inserted into a disc space D between two adjacent vertebra V1 and V2. Disposed adjacent the guide assembly 550 are vessels 562 and 560 graphically representing portions of the aorta or vena cava. Covers 556 and 558 are mounted on guide tubes 552 and 554, respectively. Flanges on the covers, shown more clearly in FIG. 15a, urge the vessels away from the guide tube and more importantly, away from working channels 553 and 555 were tools would be inserted. Vessels 560 and 562 are most closely adjacent guide tubes 552 and 554 near $V_1$. Thus, lateral extensions on the guide assembly may be insufficient to prevent contact between vessels and tools in all applications.

Figure 18:
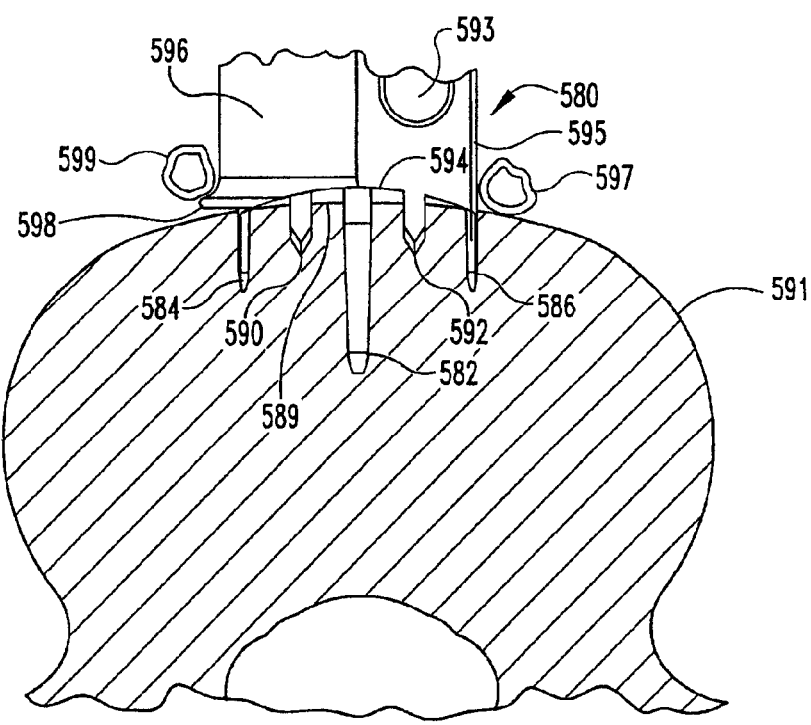
FIG. 18 is a partial cross-sectional top view of a guide sleeve assembly with only one window cover positioned thereon, a portion of the guide sleeve assembly extending into the disc space.

Referring now to FIG. 18, there is shown a top view of a guide assembly 580 positioned in the disc space adjacent a vertebral body 591. The guide assembly 580 includes a central distractor 582 and lateral extensions 584 and 586. Spikes 590 and 592 may be inserted into the bone of the vertebral body. For the purposes of illustration, cover 596 has been positioned over a first guide tube, while guide tube 595 with window 593 remains uncovered. Bone engaging end 594 does not entirely conform to vertebra surface 589, thus allowing the possibility of vessel migration into the working channels. Cover 596 with flange 598 urges vessel 599 away from the engagement between bone engaging end 594 and bone surface 589. In contrast, vessel 597 is positioned adjacent the interface between the guide tube and bone, resulting in the potential for vessel migration into the working channel via the space between the bone engaging end 594 and bone surface 589. Thus, covers according to the present invention may also be useful to further retract vessels away from the interface between the bone engaging end of the guide assembly and the bone surface.

Referring now to FIGS. 19 through 21, there is shown a reamer 200 according to the present invention. FIG. 20 shows the reamer 200 of FIG. 19 rotated 90 degrees. Reamer 200 includes a cutting head 202 having cutting flutes 203 with troughs 205 disposed therebetween. Disposed in trough 205 is an aperture 204 extending to interior channel 209. A series of apertures 204 are defined in the cutting troughs and communicate with interior channel 209. The interior of cutting head 202 is hollow and forms interior channel 209. Interior channel 209 has a first portion with side walls substantially parallel to the longitudinal axis and a second portion defined by side walls extending at an angle to the longitudinal axis. Preferably the second portion extends at a non-orthogonal angle to permit easy cleaning. The second portion is connected to aperture 208 formed on the outer surface of the shaft and spaced from the cutting head. It will be understood that aperture 208 permits material cut by reaming head 202 to move through the interior channel 209 to exit at aperture 208. Moreover, the reduced diameter segment 211 defines an area between the shaft and outer sleeve where debris from the cutting operation may collect prior to removal of the device. This collection area has a length 214 in a preferred embodiment, although it is understood that this could be extended to increase the volume of material that may be collected. This configuration permits completion of the cutting operation without a requirement to remove the reamer to clean the collected debris. Additionally, the debris may be visualized through outer sleeve windows for evaluation.

Reduced diameter shaft 211 extends proximally to tapered region 210 which expands to a larger diameter guiding portion 212. Tapered region 210 assists ease of insertion and guiding of the shaft of the reamer within an outer working sleeve as previously disclosed. Larger diameter guiding portion 212 is sized to have a reasonably close fit within an outer working sleeve to permit rotation of the device, yet limit the amount of transverse movement within the tube to insure accurate reaming within the bone. Reamer 200 may thereby be guided by a guide sleeve. Shaft 216 interconnects the proximal end to the enlarged area 212.

Disposed on shaft 216 are a series of numbers 218, which indicate the depth the reamer extends into the bone beyond the edge of a cooperable guide sleeve. As can be appreciated from examining FIGS. 19 and 20, the numbers are displayed in a stepped arrangement around the circumference of shaft 216. This stepped arrangement permits each number to be larger, in the preferred embodiment three times larger, than they could be if all numbers were listed in a single column along the device. Thus, this arrangement permits easy visualization of the number by the surgeon despite the small incremental adjustment of the device, preferably 1 mm increments. Extending more proximally along the shaft 216 are a series of grooves 221 which are adapted to engage a depth stop mechanism (described further below) to adjust the reaming depth of the device. On the proximal end 220 is a Hudson-type connection for engagement with a T-handle or other type of handle.

Figure 22:
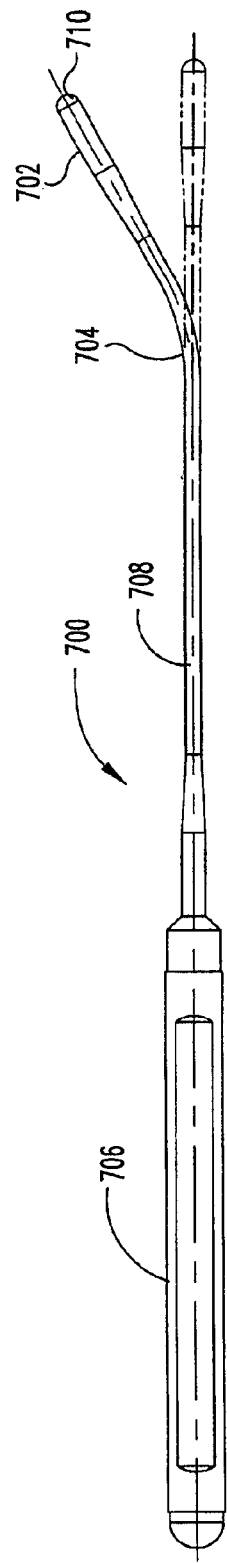
FIG. 22 is a side view of a clean out tool for use with the hollow reamer head of FIG. 19.
Figure 23:
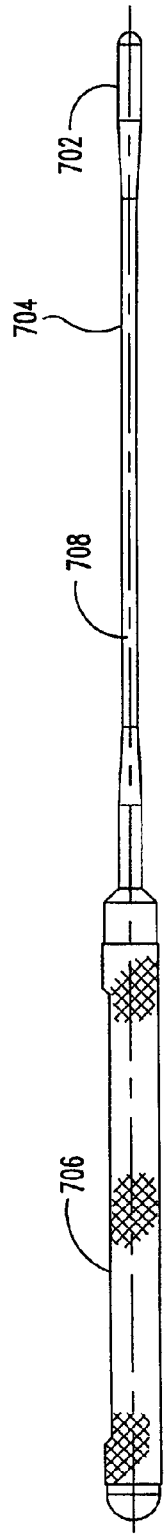
FIG. 23 is a top view of the clean out tool of FIG. 22.

Referring now to FIGS. 22 and 23, there is shown a clean out tool 700 adapted for use with the hollow reamer head described above. Clean out tool 700 includes a head 702 having a diameter substantially matching the diameter of internal chamber 209. Clean out tool 700 includes a flexible portion 704. Flexible portion 704 is connected to shaft 708 which is connected to handle 706. Flexible portion 704 allows the device to enter through opening 208 in the reamer and force material out open end 201 of the reamer head as end 710 is advanced. This is an improvement over hollow head reamers that do not provide a clean out channel.

Figure 24:
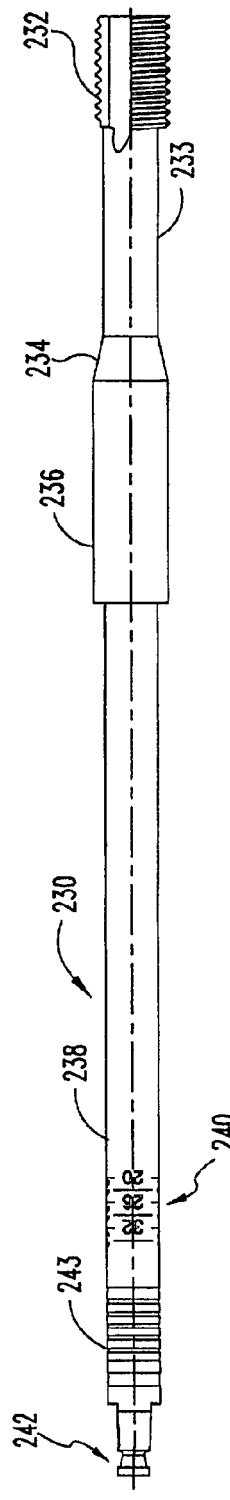
FIG. 24 is a side view of a tap in accordance with the present invention.
Figure 27:
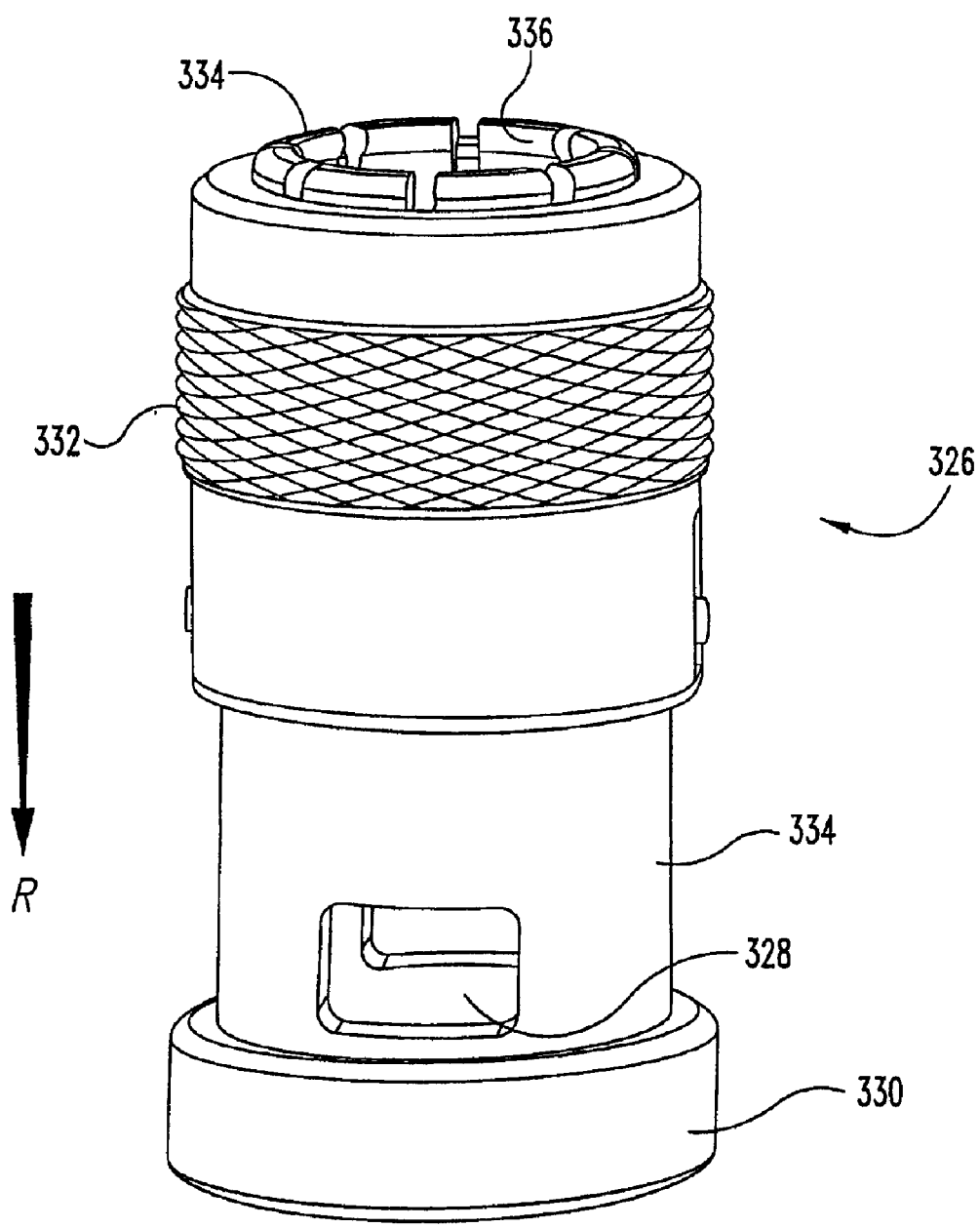
FIG. 27 is a perspective view of a depth stop according to the present invention with the collar partially retracted to expose the locking fingers.

Referring now to FIG. 24, there is shown a thread tap 230 for tapping a reamed out bone space. Tap 230 includes a cutting head 232, and a reduced diameter shaft 233 adjacent head 232 for providing space around the shaft between the outer tube for the collection of debris from the tapping operation. A tapered surface 234 extends to an increased outer diameter area 236. As previously explained with respect to reamer 200, tapered surface 232 permits guiding of the tap within a guide sleeve and enlarged area 236 by providing a reasonably close fit with the guide sleeve to maintain the axial alignment of tap 230. Tap 230 includes incrementally stepped depth markings 240 and a Hudson connection 242 as previously disclosed with respect to reamer 200.

Referring now to FIGS. 25 through 26b, there are shown modular cutting tools joined to a shaft. FIG. 25 shows a shaft 250 releasably coupled to tap head 252 by coupler 254. Similarly, shaft 250 is coupled to reamer head 256 by coupler 254. In FIG. 26a reaming head 256 may be removed from shaft 250 at the connection 254. The reamer includes a reaming head 256 having only six cutting apertures disposed around the head and a hollow internal chamber connected to aperture 258. While any number of known connection mechanisms may be used, FIG. 26b shows the use of an axially displaceable collar 260 to release balls 262 and 263 from grooves 264 and 265 of the reamer head. Shaft 250 includes a hollow extension 268 having apertures 270 and 271 to hold balls 263 and 262, respectively. Collar 260 includes a reduced diameter portion 276 adapted to urge balls 262 and 263 into grooves 264 and 265 to lock the cutting head and shaft together. Collar 260 may be axially displaced away from the cutting head to dispose an enlarged internal diameter portion 278 adjacent the balls to allow them to disengage grooves 264 and 265, thereby allowing the cutting head to be disengaged from the shaft. The same mechanism may be used with a variety of cutting heads.

Referring now to FIGS. 27 through 31, there is disclosed a depth stop mechanism cooperable with the shaft of a tool and guide sleeve such as previously disclosed. Such tools can include, without limitation, a reamer, a tap, and an implant inserter. Depth stop 326 includes an enlarged circumferential abutment shoulder 330 adapted to engage the proximal end of an outer working sleeve to prevent further advancement of the stop and any interconnected shaft. Stop 326 further includes viewing windows 328 to permit visualization of depth markings on a shaft extending within the stop. Stop 326 includes a manually operated collar 332 which may be axially displaced to allow flexing of fingers 334. Collar 332 is normally urged into an extended position by spring 342.

Referring specifically to FIG. 29, fingers 334 include projections 336 extending internally and bearing surface 337 extending externally. The internal projections 336 are configured for engagement within grooves 221 (FIG. 20) defined along a tool shaft of a working tool, and bearing surface 337 is configured to engage collar 332. Additionally, each finger includes an external taper portion 339 adapted for engagement with bearing surface 340 of collar 332 to urge the fingers inwardly as the collar is advanced. It will be understood that in a retracted position, bearing surface 340 of collar 332 will be substantially disengaged from taper 339 and permit fingers 334 to disengage from groove 221 of a working shaft (FIG. 20). With collar 332 in the extended position shown in FIG. 29, bearing surfaces 340 will bear against bearing surface 337 of each finger to urge projections 336 into grooves 221 of a tool shaft. To release fingers, collar 332 may be moved in the direction of arrow R until bearing surface 340 moves beyond tapered surface 339. The flexible fingers may then spring outward. In this manner, a user may quickly and easily disengage the locking mechanism of the stop to advance or retract a working tool and then re-engage the stop at the desired position. Preferably, distal end 333 of collar 332 will extend beyond fingers 334 to limit the possibility that surgical staff may snag protective apparel on exposed fingers.

In a first embodiment shown in FIG. 30, collar 332 is retained on housing 334 by retaining pin 342 extending into the housing and through a slot 344. Retaining pin 342 prevents rotation of collar 332 with respect to housing 334. In an alternate embodiment shown in FIG. 31, collar 332 defines an L-shaped slot 346 which permits axial displacement of collar 332 with respect to body 334, as well as a slight amount of rotation within the slot. It will be understood that the L-shaped slot 346 permits the depth stop mechanism to be locked in a disengaged position which permits free movement of the tool shaft through the depth stop. This is a desirable construction in some instances for easy removal of the depth stop from the tool shaft, as well as for utilization of the tool without the constraints of a depth stop mechanism.

Figure 32:
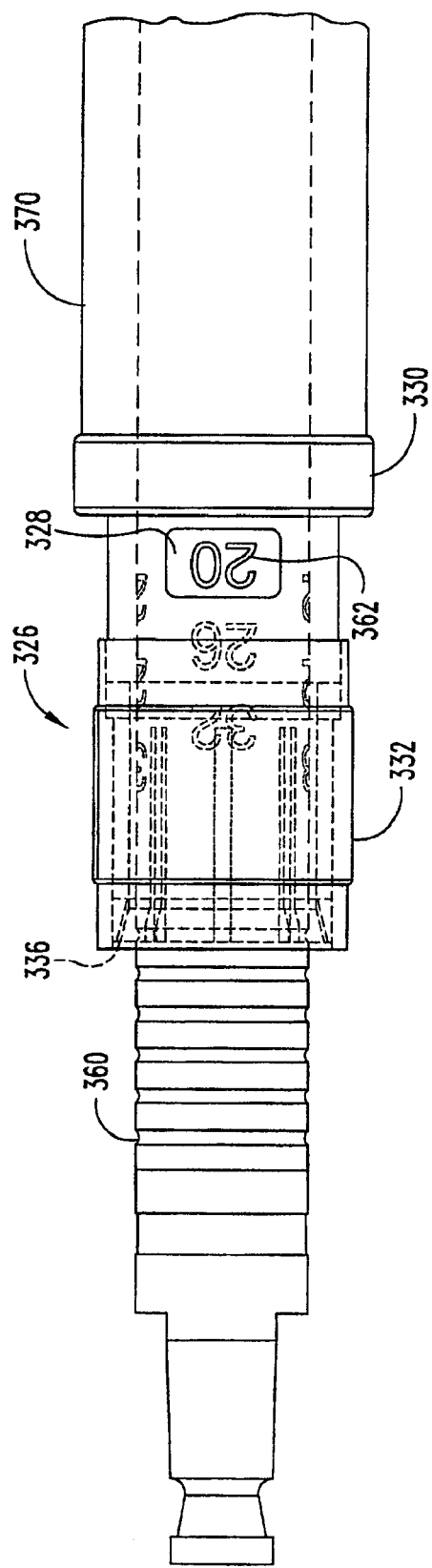
FIG. 32 is a partial side view illustrating the depth stop of FIG. 31 in engagement in with a tool shaft.

FIG. 32 shows a depth stop 326 engaged with a tool shaft having grooves 360 and marking 362 to show the depth of the distal end of the tool out of the guide sleeve 370. Abutment shoulder 330 is sized to engage the guide sleeve to prevent further movement. It will be understood that the depth of penetration may be adjusted between a number of positions defined by engagement of the fingers 336 in grooves 360 of the tool shaft. The adjustment is easily accomplished by axial movement of collar 332. Engagement with the tool shaft is indexed by the spacing of grooves 360 on the tool shaft so the exact location of the stop may be easily known. The tool shaft may be rotated with respect to the stop mechanism to display the appropriate depth numeral 362 in window 328.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A distractor, comprising:
a distraction head having a longitudinal axis and a first pair of opposed surfaces extending substantially along said longitudinal axis and defining a first working distraction height approximating a normal disc space height and a second pair of opposed surfaces extending substantially along said longitudinal axis and defining a second working distraction height approximating a second normal disc space height, with said first working distraction height being different from said second working distraction height, said distraction head rotatable between said first working distraction height and said second working distraction height by rotating said distraction head about said longitudinal axis;
wherein said distraction head includes a distractor tip having a rounded leading edge that is continuously rounded between said second pair of opposed surfaces to permit insertion of said distraction head to directly achieve said second working distraction height; and
wherein said second pair of opposed surfaces includes rounded surfaces adapted to engage and urge bone apart to said second working distraction height during rotation.

2. The distractor of claim 1, wherein said first working distraction height is 10mm and said second working distraction height is 12mm.

3. The distractor of claim 1, wherein said first working distraction height is 8 mm and said second working distraction height is 10 mm.

4. The distractor of claim 1, wherein said first pair of opposing surfaces are planar surface extending in a parallel alignment along said longitudinal axis.

5. The distractor of claim 4, wherein said distraction head includes:
a pair of inclined surfaces extending from said leading edge to said first pair of opposing surface.

6. The distractor according to claim 1, wherein said second working distraction height is greater than said first working distraction height.

7. The distractor of claim 1, further comprising a shaft joined with said distraction head.

8. The distractor of claim 7, wherein said shaft is integrally joined to said distraction head.

9. A disc space distractor, comprising:
a shaft extending along a longitudinal axis;
a distractor tip joined to said shaft;
said distractor tip including a rounded leading edge, opposing inclined surfaces and substantially planar opposing surfaces;
said rounded leading edge extending to said opposing inclined surfaces;
said opposing inclined surfaces blending into said planar opposing surfaces;
said planar surfaces extending in a parallel arrangement along said longitudinal axis to establish a first distraction height;
said distractor tip further including opposing rounded surfaces defining a second distraction height;
wherein said distractor tip is rotatable about said longitudinal axis to distract vertebrae between said first distraction height and said second distraction height;
wherein said rounded leading edge is arc shaped between the said opposing rounded surfaces to directly distract the vertebrae to said second distraction height; and
wherein said second distraction height is greater than said first distraction height.

10. The distractor of claim 9, wherein said distractor tip is integral with said shaft.

11. A distractor, comprising: a distractor tip including
a rounded leading edge,
opposing inclined surfaces extending from said rounded leading edge for easing insertion of said distractor tip into a disc space between vertebrae,
opposing planar surfaces extending in a parallel arrangement to establish a first working distraction height, said opposing inclined surfaces blending into said opposing planar surfaces,
opposing rounded surfaces extending between said opposing planar surfaces for moving the vertebrae to a second working distraction height upon rotation of said distractor tip, said second working distraction height being larger than said first working distraction height, and
said rounded leading edge having a rounded shape that forms an arc that stretches between said opposing rounded surfaces to permit direct insertion of said distractor tip into the disc space for directly achieving said second working distraction height.

12. The distractor of claim 11, further comprising a shaft coupled to said distractor tip.

13. The distractor of claim 12, wherein said distractor tip is integral with said shaft.

14. A distractor, comprising:
a distraction head having a longitudinal axis and a first pair of opposed surfaces extending substantially along said longitudinal axis and defining a first working distraction height approximating a normal disc space height and a second pair of opposed surfaces extending substantially along said longitudinal axis and defining a second working distraction height approximating a second normal disc space height, with said first working distraction height being different from said second working distraction height, said distraction head rotatable between said first distraction height and said second distraction height by rotating said distraction head about said longitudinal axis;
wherein said distraction head includes a distractor tip having a rounded leading edge that is continuously rounded between said second pair of opposed surfaces to permit insertion of said distraction head to directly achieve said second working distraction height;
wherein said first pair of opposing surfaces are planar surfaces extending in a parallel alignment along said longitudinal axis; and
wherein said distraction head includes a pair of inclined surfaces extending from said leading edge to said first pair of opposing surfaces.

15. The distractor of claim 14, further comprising a shaft joined with said distraction head.

16. The distractor of claim 14, wherein said shaft is integrally joined to said distraction head.

17. The distractor according to claim 14, wherein said second working distraction height is greater than said first working distraction height.

* * * * *